(12) United States Patent
Desjardins

(10) Patent No.: US 10,739,323 B2
(45) Date of Patent: Aug. 11, 2020

(54) INTERCONNECTING DETECTOR

(71) Applicant: Pierre Desjardins, St-Hippolyte (CA)

(72) Inventor: Pierre Desjardins, St-Hippolyte (CA)

( * ) Notice: Subject to any disclaimer, the term of this patent is extended or adjusted under 35 U.S.C. 154(b) by 0 days.

(21) Appl. No.: 16/158,488

(22) Filed: Oct. 12, 2018

(65) Prior Publication Data
US 2019/0113494 A1    Apr. 18, 2019

(30) Foreign Application Priority Data

Oct. 17, 2017  (CA) ........................... 2982648
Oct. 17, 2017  (CA) ........................... 2982661
(Continued)

(51) Int. Cl.
*G08B 3/00* (2006.01)
*G08B 5/00* (2006.01)
(Continued)

(52) U.S. Cl.
CPC ....... *G01N 33/0034* (2013.01); *G01N 33/004* (2013.01); *G01N 33/0075* (2013.01);
(Continued)

(58) Field of Classification Search
CPC ............ G01N 33/0034; G01N 33/004; G01N 33/0075; G08B 17/117; G08B 29/145; G08B 21/14
See application file for complete search history.

(56) References Cited

U.S. PATENT DOCUMENTS 4,254,414 A * 3/1981 Street .................... G08B 17/00
264/555
4,543,815 A * 10/1985 Troup .................. G01N 21/534
340/628
(Continued)

FOREIGN PATENT DOCUMENTS

CA    2920242 A1    8/2016
CN    1418358 A     5/2003
(Continued)

OTHER PUBLICATIONS

STG, Plain Dutch Weave Filter Cloth for micronic particle filtration, Aug. 17, 2016.*
(Continued)

*Primary Examiner* — Quang Pham
(74) *Attorney, Agent, or Firm* — IP Delta Plus Inc.

(57) ABSTRACT

The present detector comprises a detection level and an electronic level. The detection level comprises at least one of a smoke detection sensor, a carbon monoxide sensor and a temperature sensor. The at least one smoke detection sensor, carbon monoxide sensor and temperature sensor generate a detected measure. The electronic level includes an alarm module, a communication module and a processor. The alarm module generates at least one of an audible alarm signal or a visual alarm signal. The communication module wirelessly communicates with a monitoring central station. The processor receives the detected measure, compares the detected measure with a predetermined threshold, actuates
(Continued)

the alarm module when the detected measure is above the predetermined threshold and generates a message to be wirelessly communicated to the monitoring central station by the communication module, the message including the detected measure and a unique identifier of the detector.

20 Claims, 17 Drawing Sheets

(30) Foreign Application Priority Data

| Oct. 17, 2017 | (CA) | 2982668 |
|---|---|---|
| May 15, 2018 | (CA) | 3004952 |
| May 15, 2018 | (CA) | 3005007 |

(51) Int. Cl.

| G08B 7/00 | (2006.01) |
|---|---|
| G01N 33/00 | (2006.01) |
| G08B 29/14 | (2006.01) |
| G08B 17/117 | (2006.01) |
| G08B 25/00 | (2006.01) |
| G08B 17/10 | (2006.01) |
| G08B 21/14 | (2006.01) |
| G08B 25/10 | (2006.01) |

(52) U.S. Cl.
CPC ............ *G08B 17/10* (2013.01); *G08B 17/117* (2013.01); *G08B 25/005* (2013.01); *G08B 29/145* (2013.01); *G08B 21/14* (2013.01); *G08B 25/009* (2013.01); *G08B 25/10* (2013.01)

(56) References Cited

U.S. PATENT DOCUMENTS

| 5,053,754 | A | | 10/1991 | Wong | |
|---|---|---|---|---|---|
| 5,410,299 | A | * | 4/1995 | Hard | G08B 17/10 126/299 R |
| 5,486,811 | A | * | 1/1996 | Wehrle | G08B 17/00 340/522 |
| 5,926,098 | A | * | 7/1999 | Wiemeyer | G08B 17/113 250/573 |
| 6,285,291 | B1 | | 9/2001 | Knox | G08B 17/107 340/634 |
| 6,552,262 | B2 | * | 4/2003 | English | H02G 3/14 16/221 |
| 6,552,664 | B2 | * | 4/2003 | Nishikawa | G08B 17/103 340/517 |
| 6,624,750 | B1 | * | 9/2003 | Marman | G08B 25/003 340/4.3 |
| D485,200 | S | * | 1/2004 | Berthold | D10/106.5 |
| 6,877,895 | B2 | * | 4/2005 | Mayusumi | G08B 17/06 374/138 |
| 7,019,646 | B1 | * | 3/2006 | Woodard | G08B 17/10 340/539.26 |
| 7,034,702 | B2 | * | 4/2006 | Thomas | G08B 17/107 340/628 |
| 7,463,159 | B2 | * | 12/2008 | Hess | G08B 17/113 340/628 |
| 7,504,962 | B2 | * | 3/2009 | Smith | G08B 17/10 340/628 |
| 8,493,203 | B2 | * | 7/2013 | Egawa | G08B 17/00 340/501 |
| 8,610,587 | B2 | | 12/2013 | Tropper | |
| 8,816,867 | B2 | * | 8/2014 | Mammoto | G08B 17/10 340/632 |
| 8,970,387 | B2 | * | 3/2015 | Brigham | G08B 17/107 340/628 |
| 9,019,109 | B2 | | 4/2015 | Warmack et al. | |
| 9,075,007 | B2 | * | 7/2015 | McKendree | G01N 21/532 |
| 9,179,317 | B2 | * | 11/2015 | Thill | H04L 67/12 |
| 9,449,492 | B2 | | 9/2016 | Dixon et al. | |
| 9,659,485 | B2 | * | 5/2017 | Piccolo, III | G08B 29/145 |
| 9,836,944 | B2 | * | 12/2017 | Hwang | G01C 21/20 |
| 9,846,487 | B2 | | 12/2017 | Divakara et al. | |
| 2002/0011923 | A1 | * | 1/2002 | Cunningham | H04B 3/542 340/12.32 |
| 2003/0001746 | A1 | * | 1/2003 | Bernal | G08B 17/107 340/630 |
| 2003/0132974 | A1 | | 7/2003 | Bodin | |
| 2005/0217872 | A1 | * | 10/2005 | Oh | G08B 25/08 169/67 |
| 2005/0275528 | A1 | | 12/2005 | Kates | |
| 2011/0032109 | A1 | * | 2/2011 | Fox | G08B 25/006 340/628 |
| 2011/0215923 | A1 | | 9/2011 | Karim et al. | |
| 2012/0223646 | A1 | * | 9/2012 | Recker | G08B 5/36 315/152 |
| 2013/0033377 | A1 | * | 2/2013 | Hoseit | G08B 17/06 340/539.22 |
| 2013/0141587 | A1 | * | 6/2013 | Petricoin, Jr. | G07C 9/28 348/156 |
| 2013/0142118 | A1 | * | 6/2013 | Cherian | H04W 4/70 370/328 |
| 2014/0104067 | A1 | * | 4/2014 | Chien | G08B 17/10 340/628 |
| 2014/0121787 | A1 | * | 5/2014 | Yamazaki | G05B 19/048 700/19 |
| 2014/0335814 | A1 | * | 11/2014 | Gudlavenkatasiva | H04W 4/90 455/404.1 |
| 2015/0003475 | A1 | * | 1/2015 | Savolainen | H04L 69/324 370/474 |
| 2016/0105423 | A1 | * | 4/2016 | Logue | H04L 9/3268 726/10 |
| 2016/0284174 | A1 | * | 9/2016 | Connell, II | G08B 7/062 |
| 2017/0249819 | A1 | * | 8/2017 | Uchida | G08B 17/10 |
| 2017/0338693 | A1 | * | 11/2017 | Forbes, Jr. | H02J 3/00 |
| 2017/0345420 | A1 | * | 11/2017 | Barnett, Jr. | G06F 3/167 |
| 2018/0183874 | A1 | * | 6/2018 | Cook | H04L 43/0817 |
| 2018/0188034 | A1 | * | 7/2018 | Duan | G01C 21/206 |
| 2018/0255148 | A1 | * | 9/2018 | Kondo | H04M 11/00 |
| 2019/0294165 | A1 | * | 9/2019 | Hofmann | A62C 31/005 |

FOREIGN PATENT DOCUMENTS

| CN | 101872911 A | 10/2010 |
|---|---|---|
| EP | 1006500 A2 | 6/2000 |
| FR | 2925458 A3 | 6/2009 |

OTHER PUBLICATIONS

Investigation of the Potential Use of Blue Light in Forward Scattering Optical Smoke Chambers to Detect all UL217 Fires in the New Standard David Richardson et al. Ei Electronics, Shannon, Ireland.

* cited by examiner

INTERCONNECTING DETECTOR

TECHNICAL FIELD

The present specification relates to a detector, which communicates with a monitoring central station, and acts as a proxy for another detector connected thereto.

BACKGROUND

Smoke detectors are mandatory safety devices for residential, commercial and industrial buildings. In the first years following their introduction, residential owners and apartment dwellers used to install one battery-operated stand-alone smoke detector per home or apartment. Although better than no smoke detector, the installation of one battery-operated stand-alone smoke detector did not suffice to address on its own the problems resulting from residential fires.

The Life Safety Code® from the National Fire Protection Association 101 (NFPA 101) defines the standard for fire protection in homes. The standard has evolved over the years, and now requires that every new home be equipped with one smoke detector in every bedroom, hallway and floor. Furthermore, the standard requires that at least one smoke detector be connected to AC power, and that the smoke detectors be interconnected, so that if one smoke detector goes off, that all the smoke detectors interconnected therewith go off as well.

NFPA 101 defines the number, types and location of smoke detectors to be installed. Those guidelines include the installation of at least one AC powered smoke detector. UL/ULC™ is the organization that defines the standards and provides certification to manufacturers of electrically powered products, including smoke detectors. Since 1988, UL/ULC™ has established that all electrically powered products should be provided with a three-wire connection: a feed, a neutral and a data wire. Installation of three-wire connection electrical products, including smoke detectors, must be performed by an electrician. Thus, adding one or several UL/ULC™ smoke detectors require the services of an electrician, prohibiting further the installation of such smoke detectors.

In addition to NFPA 101's established standard and UL/ULC™ standards, Public Safety Services (PSS) recommends connecting one of the interconnected smoke detectors to a UL/ULC™ certified monitoring central station. Monitoring central stations are usually private organisations specialising in receiving and monitoring burglar and fire alarms. Properly staffed to support continuous 24 hours a day, seven days a week monitoring, these monitoring central stations receive and manage each alarm received. For example, when a smoke detector alarm signal is received at the monitoring central station, an operator of the monitoring central station may first attempt to call the home from which the smoke detector alarm signal is received, before calling a city fire department or emergency services such as 9-1-1.

However, connecting one smoke detector to a UL/ULC™ certified monitoring central station requires the addition of: a security system, 12-24 Vdc smoke detectors or one 12-24 Vdc smoke detector wirelessly interconnected with battery-operated smoke detector(s). Thus, connecting one of the interconnected smoke detectors to the UL/ULC™ certified monitoring central station is quite expensive, time consuming, and requires the further installation of a security system panel and keypad.

As NFPA 101 requires that smoke detectors be replaced every 10 years, home owners who connect their smoke detectors with one of the monitoring central stations has to replace the smoke detectors not connected to the monitoring central station as well as the smoke detector(s) connected to the monitoring central station, thus increasing the costs of such replacements.

U.S. Pat. No. 9,875,631 describes a two-wire smoke detector that is AC powered, includes batteries for power outages period, and includes a Wi-Fi communication unit. However, the two-wire electrical connection of this two-wire smoke detector lacks the mandatory requirement of third wire interconnection set by UL/ULC™, and therefore cannot be used to replace existing electrically powered smoke detectors in homes built after 1988. Furthermore, the two-wire smoke detector described in U.S. Pat. No. 9,875,631 relies on a proprietary electrical power connector that is incompatible with existing connectors and requires the replacement of the existing power harnesses by a qualified electrician. Moreover, the Wi-Fi communication unit described sends text messages to a smartphone and cannot be connected a UL/ULC™ monitoring central station. Furthermore, as 49% of home fires involved an electrical failure, and most Wi-Fi users do not protect their Internet equipment with a battery back-up, the Wi-Fi connection proposed by U.S. Pat. No. 9,875,631 is not sufficiently reliable and does not alleviate many of the current problems.

BRK™ offers through its SA520B series a wireless alarm-bridge electrically powered detector including a wire and wireless interconnection. However, the SA520B series is not adapted for transmitting alarms to a UL/ULC™ monitoring central station.

There is therefore a need for an AC three-wire powered and interconnectable detector, adapted to communicate with a UL/ULC™ certified monitoring central station.

There is also a need for a detector which is compatible with current electric power harnesses, therefore alleviating the need to hire an electrician for installation.

There is also a need for a detector which reduces the number of false alarms.

SUMMARY

According to a first aspect, the present disclosure relates to a detector comprising a detection level and an electronic level. The detection level comprises at least one of a smoke detection sensor, a carbon monoxide sensor and a temperature sensor. The at least one smoke detection sensor, carbon monoxide sensor and temperature sensor generate a detected measure. The electronic level includes an alarm module, a communication module and a processor. The alarm module generates at least one of an audible alarm signal or a visual alarm signal. The communication module wirelessly communicates with a monitoring central station. The processor receives the detected measure, compares the detected measure with a predetermined threshold, actuates the alarm module when the detected measure is above the predetermined threshold and generates a message to be wirelessly communicated to the monitoring central station by the communication module, the message including the detected measure and a unique identifier of the detector.

BRIEF DESCRIPTION OF THE DRAWINGS

Embodiments of the disclosure will be described by way of example only with reference to the accompanying drawings, in which.

DETAILED DESCRIPTION

The foregoing and other features will become more apparent upon reading of the following non-restrictive description of illustrative embodiments thereof, given by way of example only with reference to the accompanying drawings. Like numerals represent like features on the various drawings.

Various aspects of the present disclosure address the drawbacks of current detectors, and more particularly, the needs for having a detector that communicates directly with a monitoring central station.

The following terminology is used throughout the present disclosure:

Detector: Means any of a smoke detector, a carbon monoxide detector, or a combined smoke and carbon monoxide detector.

Monitoring central station: Means any of a surveillance station, an emergency dispatch office, public-safety answering point, fire stations, proprietary web service, etc.

Residence: a building or area in a building for human occupation or activities, such as for example a house, a condo, an apartment, an office, a store, a warehouse, etc.

Figure 1:
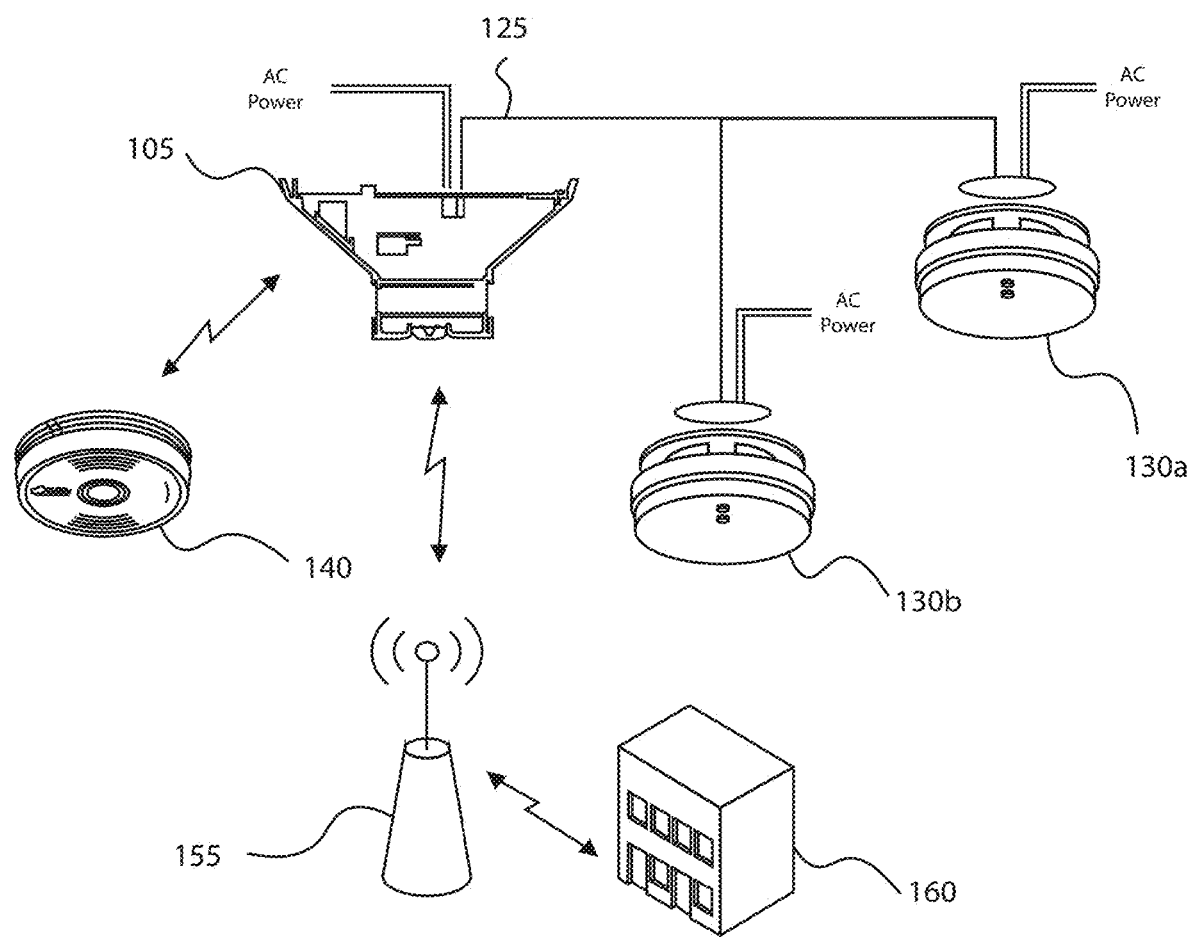
FIG. 1 an exemplary installation of a detector 105 in accordance with the present invention

Referring to FIG. 1, there is depicted a detector 105 in accordance with an exemplary installation. The exemplary installation is for illustration purposes only and could include more or less components as well as different types of components, without departing from the scope of the present description. The exemplary installation comprises a detector 105. In the exemplary installation shown on FIG. 1, the detector 105 is shown as being electrically connected to a data link 125 shared with two detectors 130a and 130b. The exemplary installation may further comprise a wireless detector 140 which wirelessly communicates with the detector 105. Although not shown on FIG. 1, the detector 105 could be a stand-alone detector. In the exemplary installation shown on FIG. 1, the detector 105 communicates over cellular link to a cellular network access point 155 such as a cellular antenna. The detector 105 communicates with the cellular network access point 155 using any known cellular technology such as 2G, 3G, 4G, 5G, LTE, GSM etc. The cellular network access point 155 communicates directly or indirectly through an Internet network with a monitoring central station 160.

The detectors 105, 130a and 130b are depicted as each receiving AC power from an AC power source, while the detector 140 is shown as being battery powered. However, each or all of the detectors 105, 130a, 130b and 140 could be either powered by AC, battery, or a combination of AC and battery.

Figure 2:
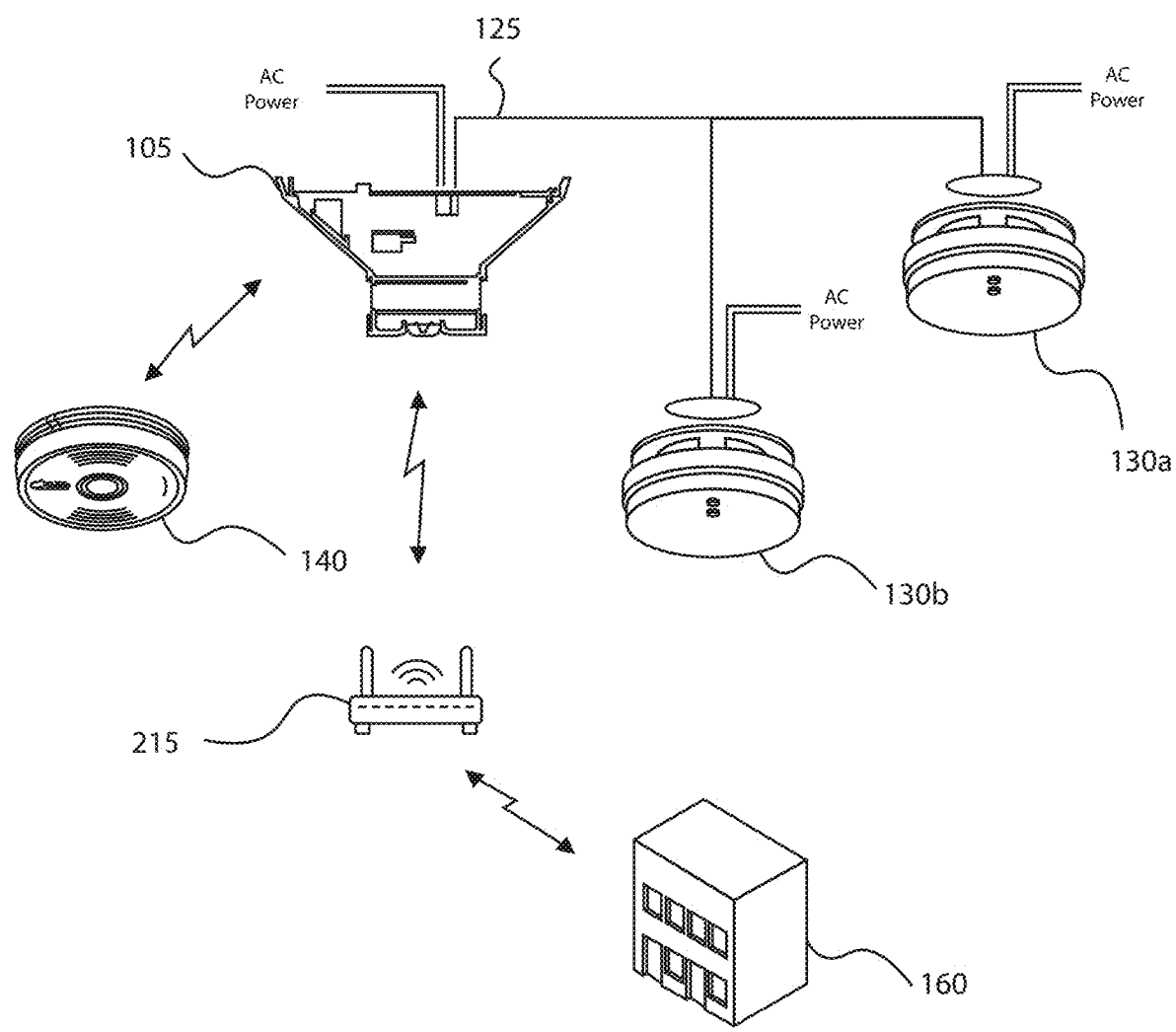
FIG. 2 is another exemplary installation of the detector 105.

Referring to FIG. 2, another exemplary installation of the detector 105 is shown. In the exemplary installation of FIG. 2, the detector 105 communicates with the monitoring central station 160 over a Wi-Fi connection through a wireless network access point 215. The detector 105 communicates with the wireless network access point 215 using any known data protocol such as for example Wi-Fi technology (i.e. 802.11, 802.11a, 802.11b, 802.11g, 802.11n, 802.11ac etc.) or any other standardized or proprietary data protocol. The detector 105 may communicate with the wireless network access point 215 using a secured data protocol such as for example: encryption and/or Virtual Private Network. The wireless network access point 215 communicates with the monitoring central station 160 using an IP protocol such as for example IPv4, IPv6 of any other similar protocol which can be carried over an Internet Network.

Figure 3:
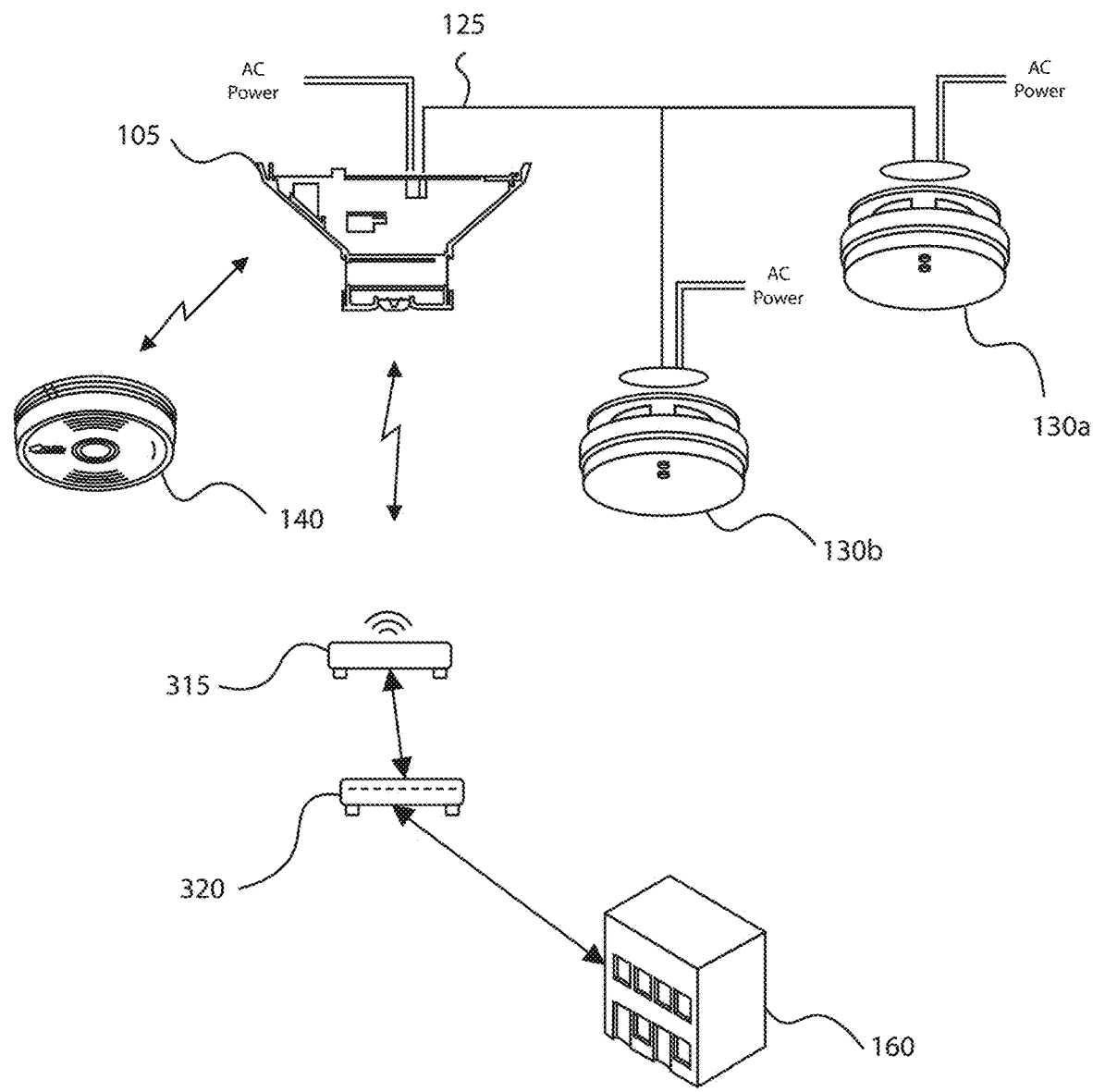
FIG. 3 is yet another exemplary installation of the detector 105.

Referring to FIG. 3, there is shown yet another exemplary installation of the detector 105. In the exemplary installation of FIG. 3, the detector 105 communicates over a wireless proprietary connection with a proprietary wireless network access point 315. The proprietary wireless network access point 315 may communicate wirelessly with the monitoring central station 150 or may be hardwired to an internet router 320 for wired communication with the monitoring central station 160. The internet router 320 communicates with the monitoring central station 160 using an IP protocol such as IPv4, IPv6 of any other similar protocol which can be carried over an Internet Network. Alternatively, the detector 105 may communicate using any other RF technology which is secured and standardized.

Although the exemplary installations depicted in FIGS. 1-3 are illustrated as three separate exemplary installations, the present description is not limited to such three exemplary installations. The depicted exemplary installations could be combined or grouped so as to provide several variants of the exemplary installations.

Figure 4:
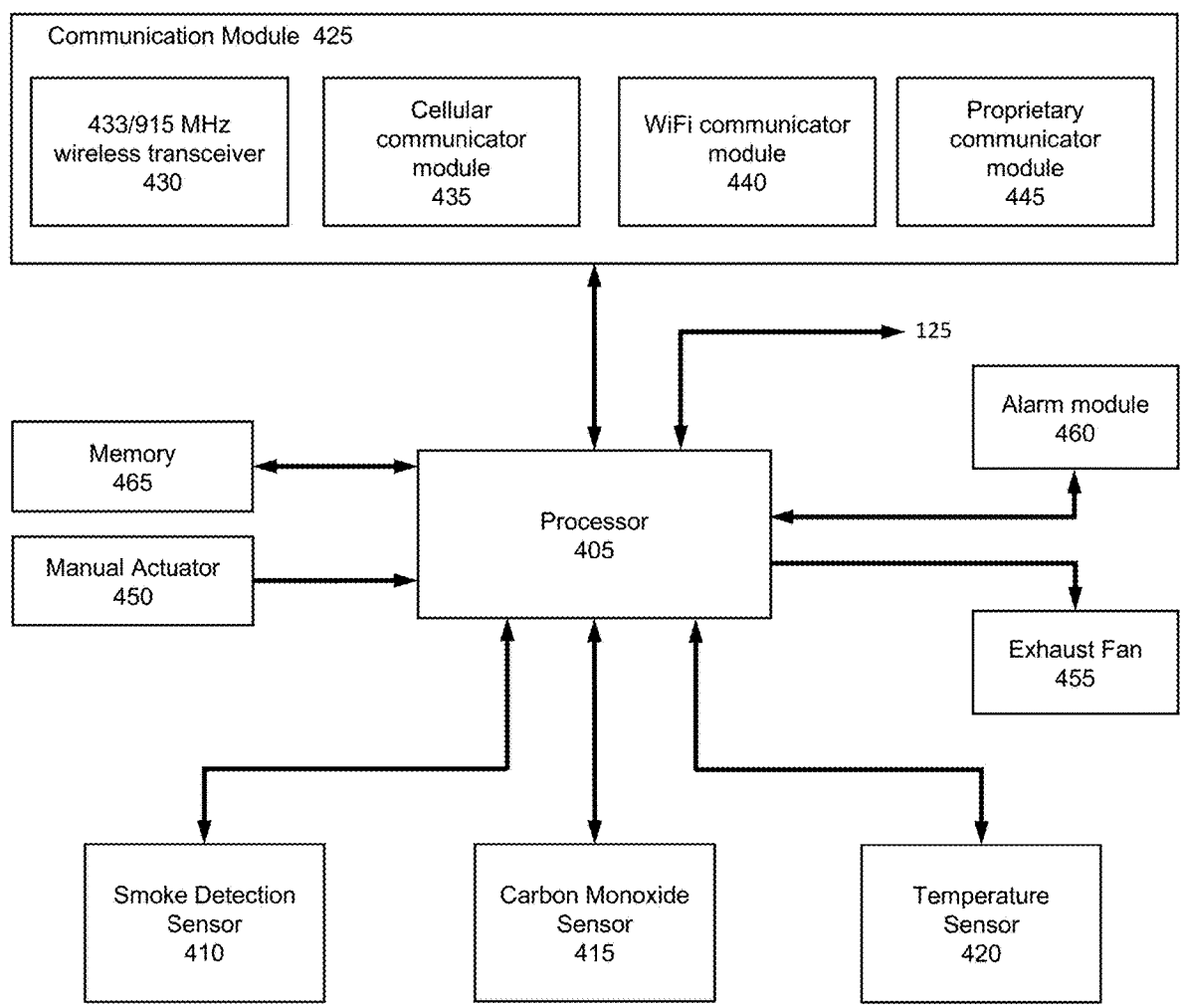
FIG. 4 is a block diagram of modules of the detector 105.

Reference is now made concurrently to FIGS. 1-4, where FIG. 4 shows a block diagram of modules of the detector 105. The detector 105 comprises a processor 405, a memory 465, a communication module 425 and at least one of: a smoke detection sensor 410, a carbon monoxide sensor 415, and a temperature sensor 420. The detector 105 further comprises a manual actuator 450, an exhaust fan 455 and an alarm module 460. The communication module 425 comprises a 433/915 MHz wireless transceiver 430, and at least one of the following modules: a cellular module 435, a Wi-Fi module 440 and a RF proprietary module 445.

Figure 5:
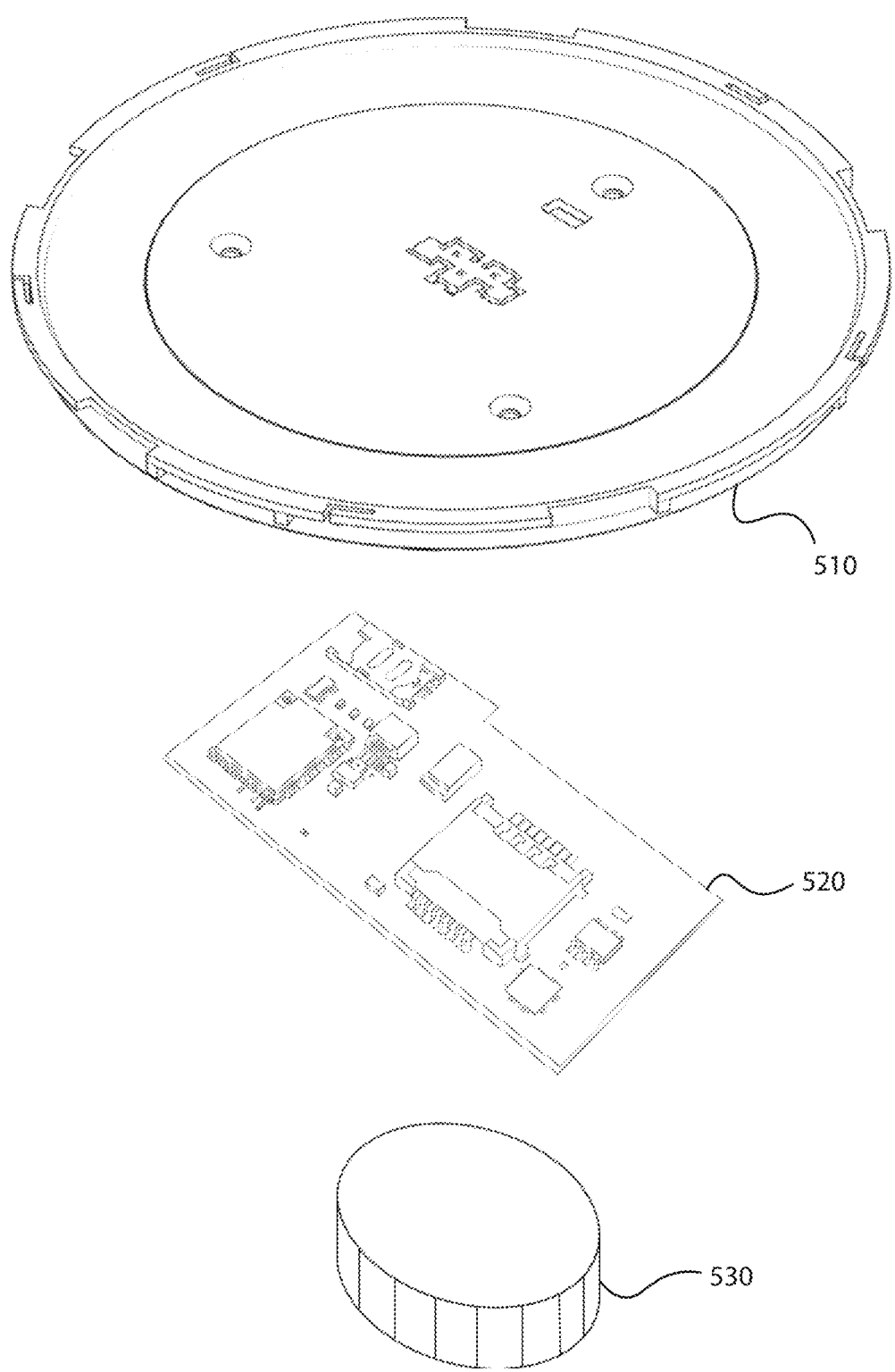
FIG. 5 is an exploded view of level of components of the detector 105.

Reference is now further made to FIG. 5, which is an exploded view of exemplary hardware implementation of the detector 105. FIG. 5 is not intended to provide a detailed list of components or hardware implemented in the detector 105, but an introduction to levels of hardware of the detector 105. The detector 105 typically comprises three levels of components: an electric connection level 510, an electronic level 520 and a detection level 530. The at least one smoke detection sensor 410, a carbon monoxide sensor 415 and temperature sensor 420 are part of the detection level 530. The exhaust fan 455 is also implemented adjacent to the at least one smoke detection sensor 410, carbon monoxide sensor 415 and temperature sensor 420 in the detection level 530. The electronic level 520 comprises the processor 405, the memory 465, the communication module 425, the manual actuator 450, and the alarm module 460. The electric connection level 510 comprises the hardware for connecting the detector 105 to an AC power source, and to electrically connect to hardwired detectors 130*a* and 130*b*. The representation in three levels, namely the electric connection level 510, the electronic level 520 and the detection level 530 is meant to facilitate understanding of the operation of the present detector 105 and should not be interpreted as limiting the possible implementations of the present detector 105. For example, each of the manual actuator 450 and the alarm module 460 could alternatively be implemented in the detection level 530 or the electric connection level 510 without departing from the present invention.

Electric Connection Level 510

Figure 6:
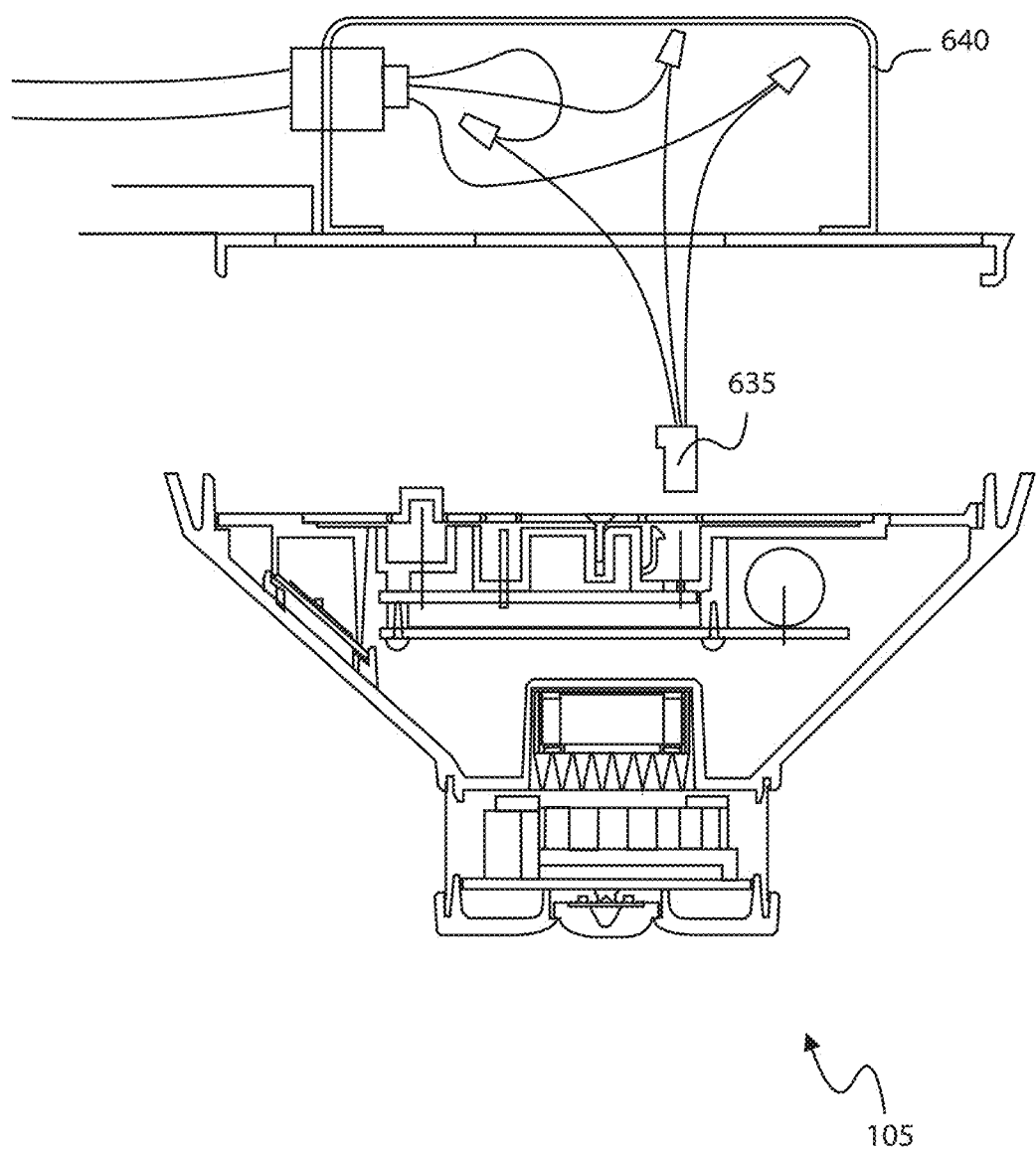
FIG. 6 is a cross-sectional view of an exemplary implementation of the detector 105.

Reference is now further made to FIG. 6, which is a cross-sectional view of an exemplary implementation of the detector 105 placed adjacent to an electrical box 640. FIG. 6 is not meant to illustrate all the components of the electric connection level 510, the electronic level 520 and detection level 530, but provides an overall cross-section representation of certain aspects of the detector 105.

When installing a prior art detector, an electrician connects a connector 635 to perform the electrical connection between the AC power, the hardwired detectors 130*a* and 130*b* and the prior art detector. The connector 635 includes three wires: a positive, a neutral and a data wire. One of the difficulties lies in the lack of standard in the connectors 635 provided by manufacturers. To ensure customer loyalty, manufacturers design their own connectors 635. Thus connectors 635 from different manufacturers have different shapes and adapters are needed to allow compatibility between the connector 635 in the electrical box 640 and the detector 105. It is possible to ask an electrician to come change the connector 635 installed in the electrical box 640, but such an operation is costly. Another option is to buy and add an adapter between the connector 635 and the detector 105. However, it is not possible to know beforehand which adapter is required. Furthermore, the electrical box 640 is often already quite crowded, and adding an adapter between the connector 635 and the detector 105 may result in overheating electrical wires, which is also not desirable.

Figure 7A:
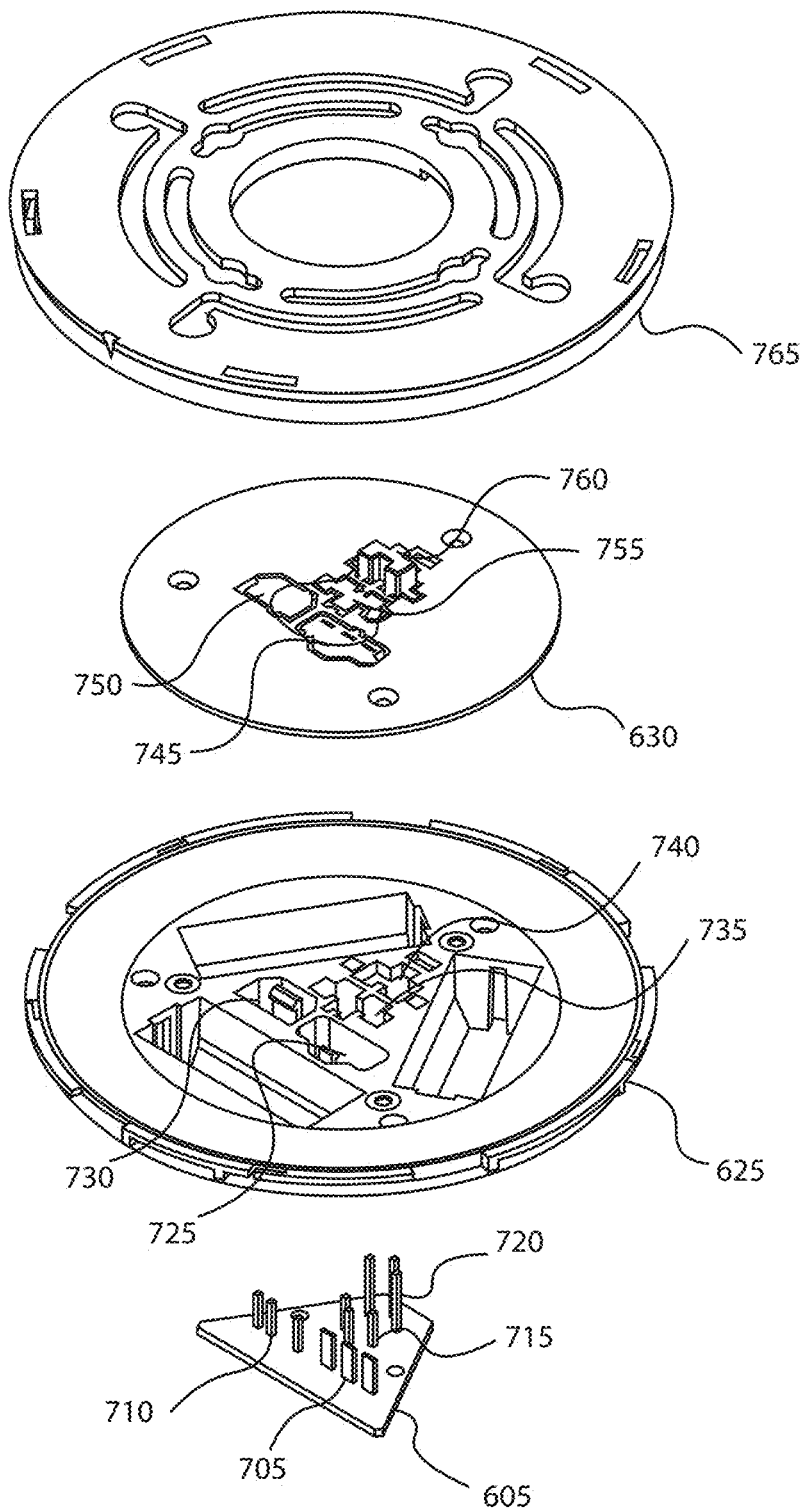
FIG. 7A is an exploded perspective view of the electric connection level 510.

To overcome this incompatibility problem, the electric connection level 510 of the present detector 105 provides an innovative solution: multiple active mating connectors. Reference is now further made to FIG. 7A, where FIG. 7A is an exploded perspective view of the electric connection level 510 of the detector 105. The electric connection level 510 comprises a connector plane 605 and a connector plate, where the connector plate has a lower section 625 and an upper section 630. The connector plane 605 provides a plurality of conducive 3-pin sets 705, 710, 715 and 720. Each pin set is dedicated to one particular type of connector 635. Thus each 3-pin set 705, 710 and 715 allows independent connection of the detector 105 to the AC power source and the data link 125 shared with the hardwired detectors 130*a* and 130*b*.

The electric connection level 510, and more precisely the connector plane 605 of the electric connection level 510 powers the electronic level 520 and the detection level 530. The connector plane 605 also connects the hardwired detectors 130*a* and 130*b* to the processor 405. The connector plane 605 is inserted within the lower section 625 of the connector plate. The lower section 625 of the connector plane defines a plurality of connector receptacles 725, 730, 735 and 740. Each connector receptacle 725, 730, 735 and 740 has a set of apertures for receiving therethrough one of the sets of conducive pins of the connector plane 605.

The lower section 625 of the connector plate comprise at least two connector receptacles 725, 730, 735 and 740 for receiving at least two mating connectors 745, 750, 755 and 760 for the following types of connector 635: a legacy Kidde™ pigtail, a 2014 or more recent Kidde™ pigtail, a Firex™ pigtail, a BRK™ pigtail, a First Alert™ pigtail, a Dicon™ pigtail and an American Sensor™ pigtail. The upper section 630 of the connector plate comprises the at least two mating connectors 745, 750, 755 and 760. The at least two mating connectors 745, 750, 755 and 760 are in electrical connection with the connector plane 605.

Figure 7B:
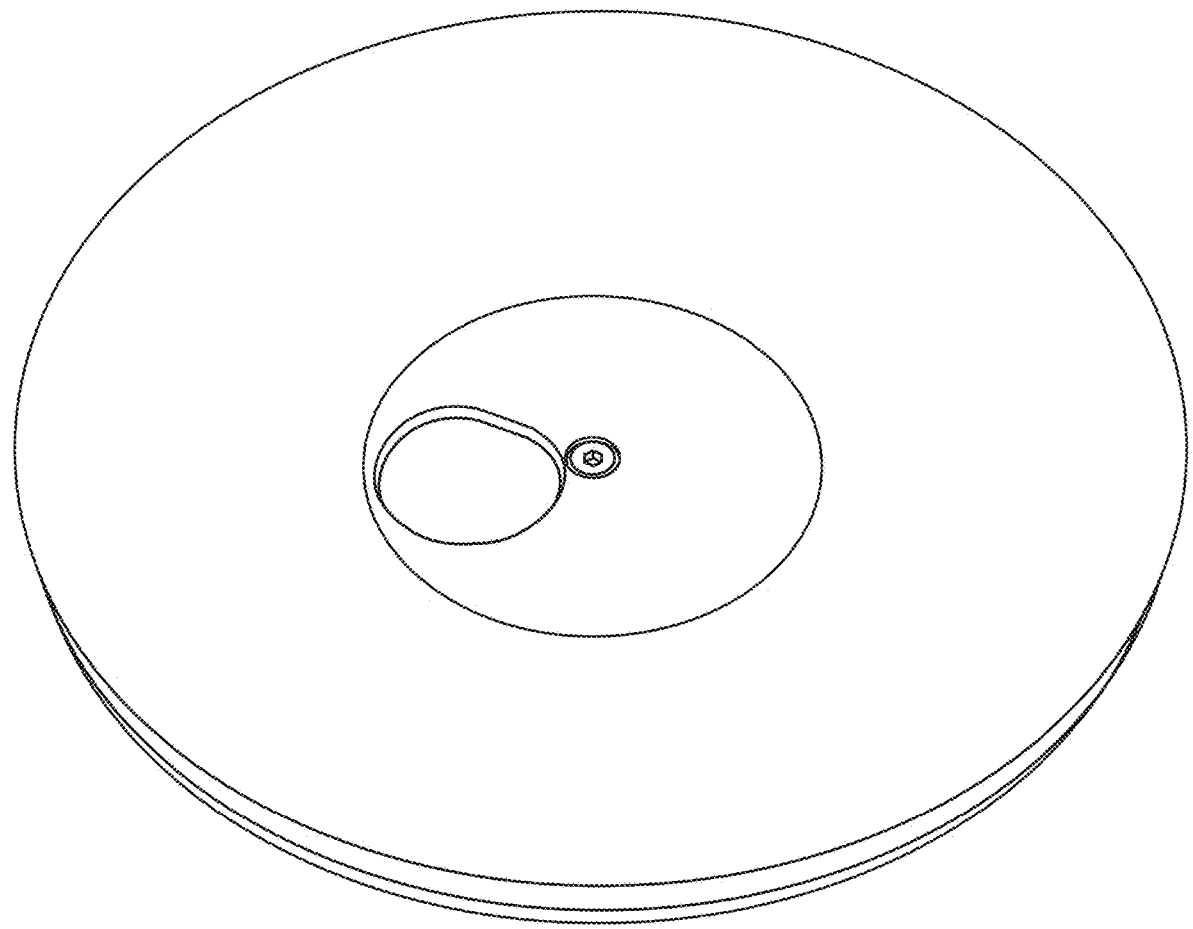
FIG. 7B is a perspective view of another exemplary implementation of the electric connection level 510.

The upper section 630 of the connector plate is a mechanical protection mechanism for allowing access to only one of the mating connectors 745, 750, 755 and 760 at a time. The mechanical protection mechanism may for example consists of breakaway sections of the upper section 630 of the connector plate, where each breakaway section gives access to one of the mating connectors 745, 750, 755 and 760. In another example shown on FIG. 7B, the upper section 630 of the connector plate is provided with a mating connector aperture. The upper section 630 of the connector plate is rotatably affixed to the lower section 625 of the connector plate and is rotated with respect to the lower section 625 of the connector plate so as to align the mating connector aperture with only one of the mating connectors 745, 750, 755 and 760 at a time. Alternatively, the upper section 630 of the connector plate comprises an articulated door (not shown) which provides access to only one of the mating connectors 745, 750, 755 and 760 at once. The articulated door may be rotated, slide or hinged with respect to the lower section 625 of the connector plate, so as to provide access to only one mating connector 745, 750, 755 and 760 at a time.

The upper section 630 of the connector plate is secured to the lower section 625 of the connector plate so as to prevent tampering and accessing more than one mating connector 745, 750, 755 and 760 at a time.

The electric connection level 510 is further adapted to be affixed to a holding plate 765. The holding plate 765 is affixed to the electrical box 640 and receives the upper section 630 of the connector plate.

Figure 8:
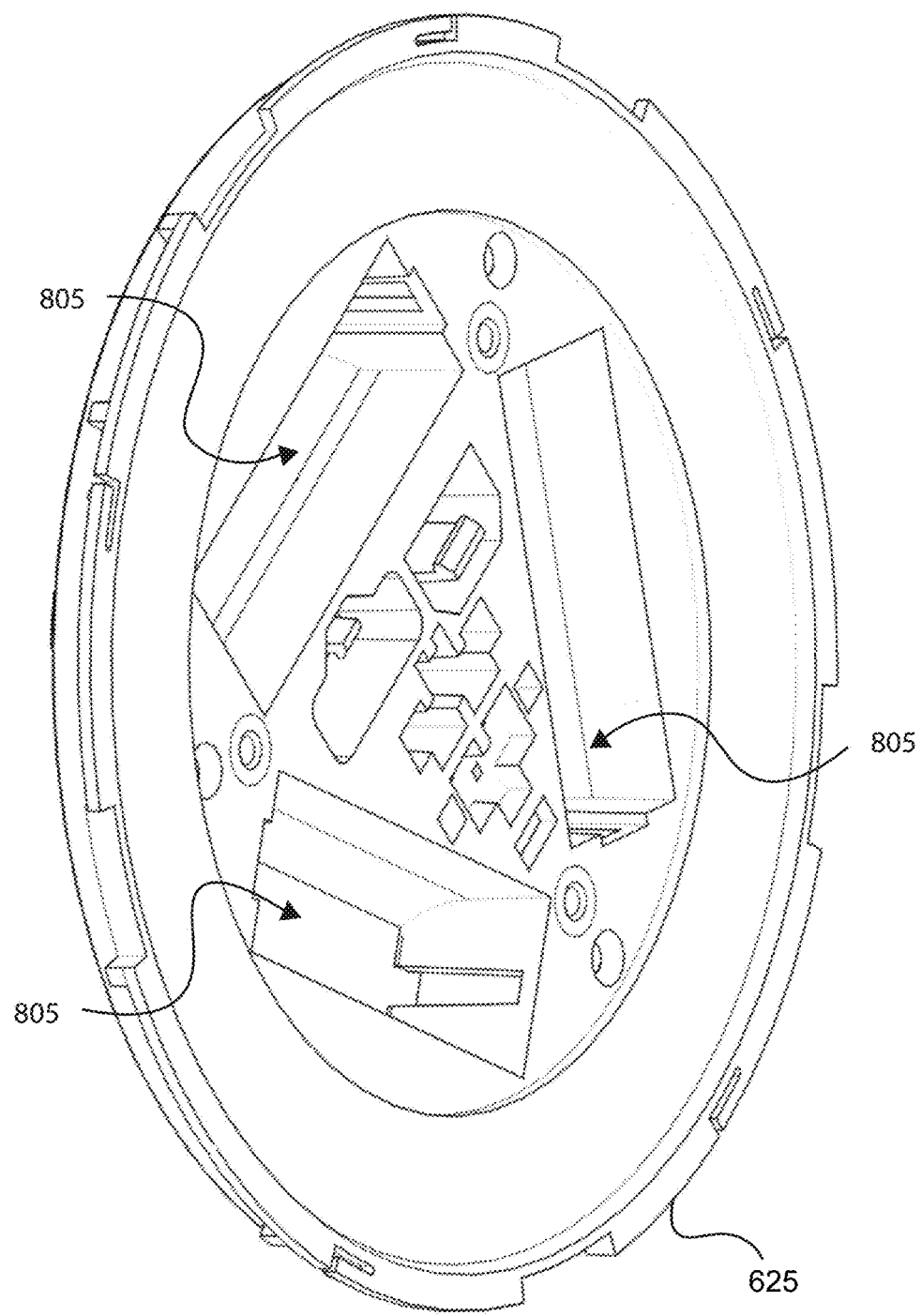
FIG. 8 is an enlarged perspective view of a lower section 625 of a connector plate.

Referring to FIG. 8, the lower section 625 of the connector plate is further provided with battery receptacles 805 for receiving batteries (not shown) to power the detector 105. The batteries are in electrical contact with the connector plane 605 so as to provide electrical power to the electronic level 520 and the detection level 530. The batteries may power the detector 105 during AC power outage periods or be the main source of electric power for the detector 105 for 10 years.

Detection Level 530

Most certification standardization authorities require that detectors be installed at or near a ceiling, so as to be out of reach. Because of the difficulty inherent to easily reaching so high, most residents never clean their detectors. This results in dust accumulation around the detection level 530 and inside the detection level 530, thereby reducing the efficiency of the detector 105 and causing false alarms, i.e. presence of particles that results in triggering false alarms.

For example, CAN/ULC-S531-14, a well-known certification standardization authority in the detector industry, requires that detectors be provided with an insect guard for preventing entry of insects as small as 1.27 mm. However, certification standardization authorities do not require filters for particles smaller than 1.27 mm. To prevent some dust and mist particles to enter the detector and the triggering of false alarms, some manufacturers rely on insect guards with openings ranging from 0.1 mm to 1.27 mm.

Smoke particles, which are the particles which trigger positive alarms, measure from 0.01 um to 10 um. In contrast, studies such as the article "Isolation and characterization of a respirable particle fraction from residential house-dust" written by Asa Gustafsson, Annette M. Krais, András Gorzsás, Thomas Lundh and Per Gerde published in February 2018 in the Environmental Research, volume 161 pages 284-290 have determined that 89.2% of dust particles measure more than 25 um, and 68.2% of dust particles measure more than 500 um. Thus, prior art detectors only filter 68% of the dust particles, letting 32% of the dust particles inside the detectors.

Another contributing factor reducing the efficiency of prior art detectors is mist. When a prior art detector is placed nearby a shower, especially during high humidity season or during winter season when windows are closed, the shower produces mist that enters the detection level and sometime triggers a false alarm.

Prior art detectors rely on straight weave filters for preventing entry of particles of 500 microns (um) or more, and do not properly filter mist or dust particles, thereby causing undesirable false alarms.

Figure 9:
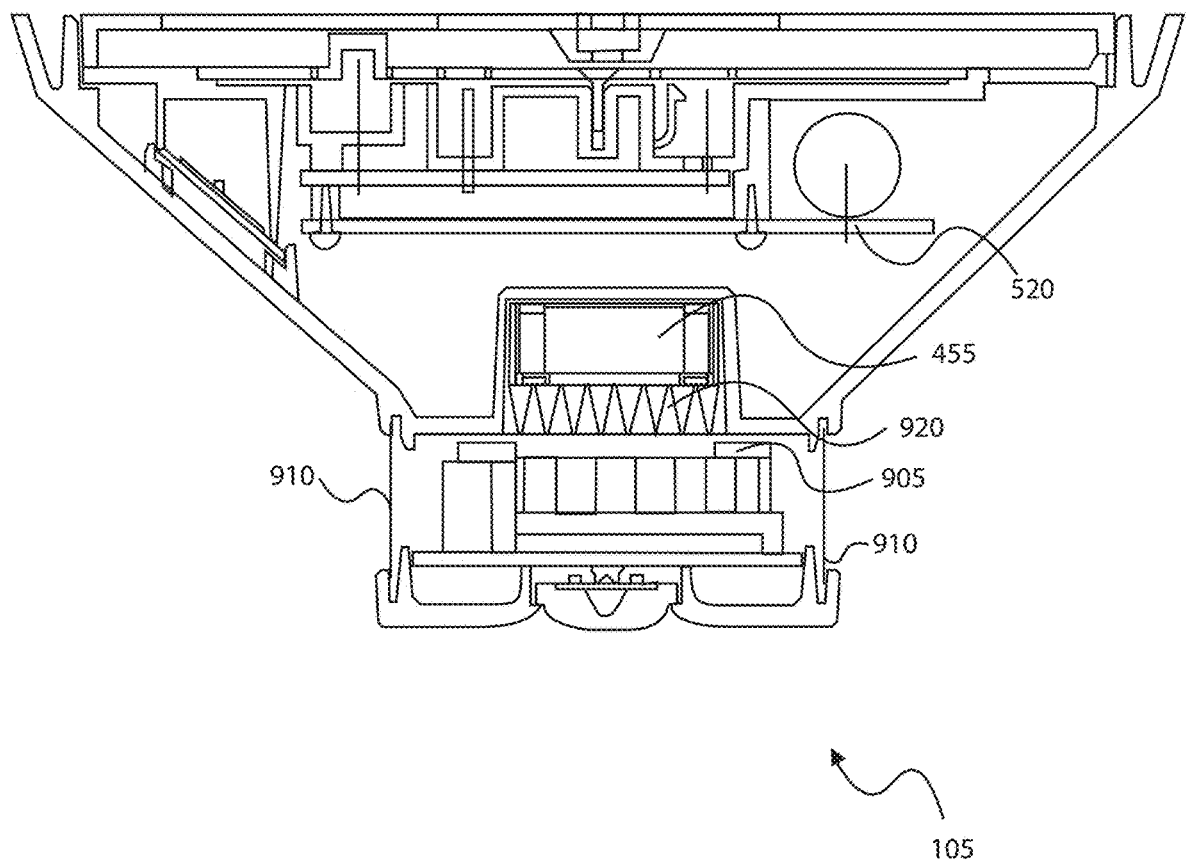
FIG. 9 is a cross-sectional side elevation view of the detector 105.
Figure 10:
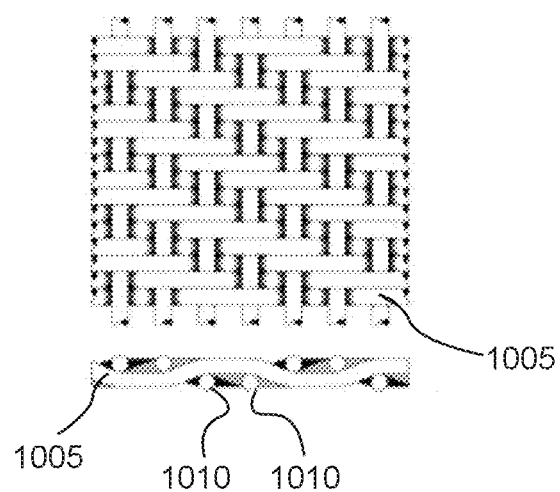
FIG. 10 is a plan view of a Dutch weave wire cloth 910.
Figure 11:
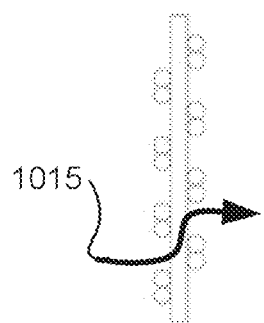
FIG. 11 is a side elevation view of the Dutch weave wire cloth 910 shown in FIG. 10.

The present detector 105 alleviates the problems of prior art detectors by relying on a different type of filter 910, i.e. using a Dutch weave wire cloth filter for filtering dust and mist. Reference is now concurrently made to FIGS. 9, 10 and 11, where FIG. 9 is a cross-sectional side elevation view of the detector 105, FIG. 10 is a plan view of an example of Twill Dutch weave wire cloth 910 and FIG. 11 is a side elevational view of the Twill Dutch weave wire cloth 910 shown on FIG. 10.

The detector 105 comprises a detection chamber 905 surrounded by the Dutch weave wire cloth filter 910. The Dutch weave wire cloth filter 910 blocks mist and dust particles, thereby preventing false alarms. Dutch weave wire cloths are typically offered as plain Dutch weave and twill Dutch weave. The twill Dutch weave wire cloth has been tested with the present detector 105 and has proven very efficient at filtering dust and mist, and thereby reducing the number of false alarms.

Dutch weave wire cloth filters particles under a chosen diameter (15 um in the tests performed). By surrounding the detection chamber 905 with the Dutch weave wire cloth filter 910 of 15 um, about 89.5% of dust could be filtered efficiently. Considering smoke size particles measure between 0.01 to 10 um, surrounding the detection chamber 905 with the Dutch weave wire cloth filter 910 filters better dusts than any known filter used in prior art detectors, without jeopardizing the efficiency of smoke particles detection.

The Dutch weave wire cloth filter 910 may be made of stainless steel, anodized steel, aluminium, fabrics or any other rust-proof material adapted to be weaved so as to form microscopic holes smaller than most dust and mist particles (i.e. few microns).

The Dutch weave wire cloth filter 910 provides an additional non-negligible benefit over prior art filters. The metallic Dutch weave wire cloth filter 910 (such as for example the stainless steel) remains colder than its surroundings. Thus, when mist particles (warmer than air) get in contact with the Dutch weave wire cloth filter 910 (colder than air), the Dutch weave wire cloth filter 910 cools down the mist particles, thereby transforming the mist particles into microdroplets which condense around an exterior surface of the Dutch weave wire cloth filter 910.

The Twill Dutch weave wire cloth filter 910 is a particular type of weaving which combines Dutch and Twill weavings. Shute wires 1005 are passed over and under two warp wires 1010, providing a tight, fine Dutch weave wire cloth 910 with tapered openings. The tapered openings of the Dutch weave wire cloth 910 prevent particles 1015 larger than the tapered openings from passing through the weave, while allowing particles smaller than the tapered openings to pass through the Dutch weave wire cloth filter 910.

The Twill Dutch weaving process allows for the use of very fine wires, i.e. in the micron range, producing wire cloths that let smoke particles of 0.01 to 10 microns pass through while blocking undesirable particles of 10 microns and higher. Furthermore, Twill Dutch wire cloth can be weaved flat, partially rugate or totally rugate. The partial or total rugate weave provide a greater wire surface exposition, resulting in higher filtering capacity. In the tests performed, the partial and total rugate weaves have proven be more efficient than the flat weave in filtering dust and mist particles, while allowing passage of smoke particles.

In addition to false alarms caused by dust and mist, false alarms may also be caused by minor and temporary particles (for example toaster, shower, hair spray, etc.) and/or dust accumulated on the exterior surface of the filter of the detection chamber 905 or accumulated inside the detection chamber 905.

Figure 12:
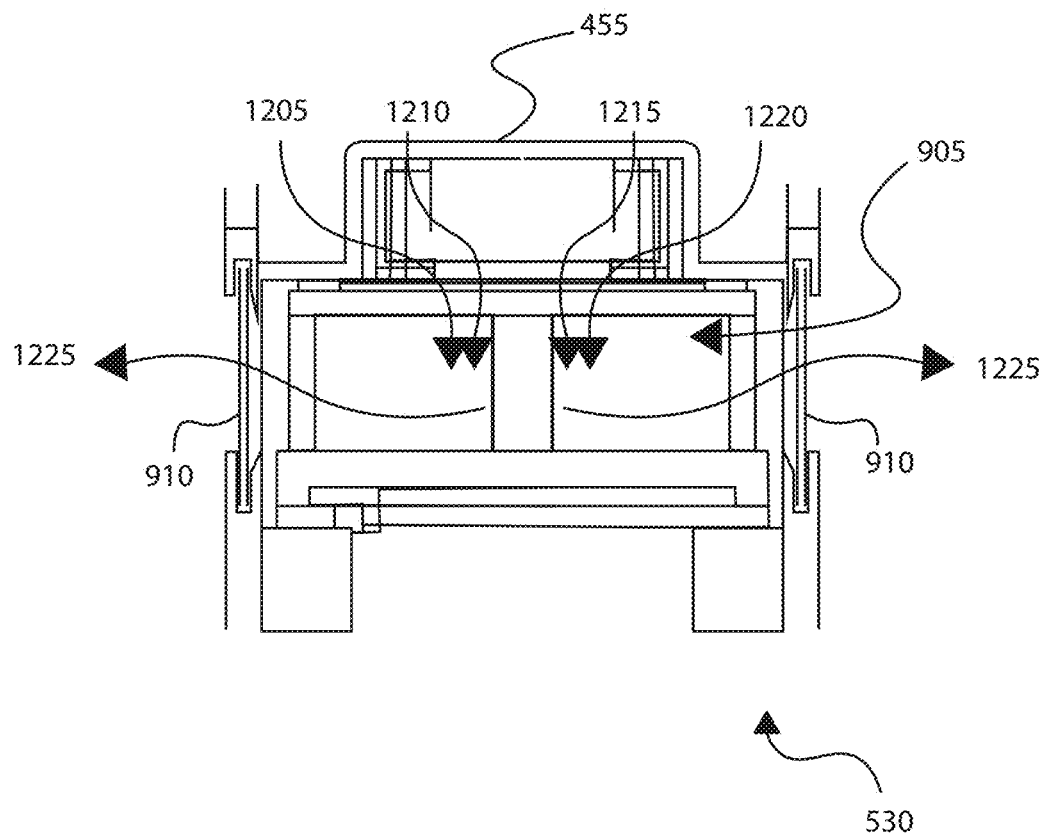
FIG. 12 is partial cross-sectional side elevation view of the detection level 530 and a purging air flow.

Reference is now further concurrently made to FIGS. 4, 9 and FIG. 12, where FIG. 12 is a partial cross-sectional side elevation view of the detection level 530 and purging air flow. The present detector 105 may further or alternately address the problems associated with false alarms and how such false alarms are handled by actuating the exhaust fan 455 to purge the detection level 530, and more particularly the detection chamber 905 and an exterior surface of the filter 910. The exhaust fan 455 is located between the detection level 530 and the electronic level 520. More particularly, the exhaust fan 455 is located inside the detector 105 and is positioned above the detection chamber so that the exhaust fan 455 can push air through the detection chamber 905 and purge the content of the detection chamber 905 while forcing air through the filter 910 so as to remove any dust or debris accumulated on an exterior surface of the filter 910.

The exhaust fan 455 is controlled by the electronic level 520, and more particularly the processor 405 of the electronic level 520. The processor 405 controls the actuation of the exhaust fan 455. The processor 405 further controls scheduled actuation of the exhaust fan 455 to periodically purge the detection chamber 905 so as to prevent accumulation of dust and minor and temporary particles inside the detection chamber 905, as well as on the exterior surface of the filter 910. The exhaust fan 455 may further be manually actuated. The processor 405 may further control the speed of the exhaust fan 455. Operation of exhaust fan 455 by the processor 405 and the manual actuation will be described further.

To prevent introducing debris in the detection chamber 905 when performing a purge by the exhaust fan 455, an exhaust filter 920 is provided. The exhaust filter 920 filters the air that is used to purge the detection chamber 905. The exhaust filter 920 may be any type of filter known in the art for filtering air or may be similar to the filter 910.

Positioning of the exhaust fan 455 above the detection chamber 905 serves another purpose. During operation, smoke particles or carbon monoxide enter the detector 105 through the filter 910 and accumulate into the detection chamber 905. As the exhaust fan 455 and the exhaust filter 920 are strategically positioned above the detection chamber 905, smoke particles have not yet reach or are just starting to reach the exhaust fan 455.

When the processor 405 determines that the detected measure received from one of the smoke detection sensor 410, the carbon monoxide sensor 415 and the temperature sensor 420 are above the predetermined threshold, the processor 405 may actuate the exhaust fan 455 for a predetermined period of time so as to purge the detection chamber 905 and push debris accumulated on the exterior surface of the filter 910.

When actuated, the exhaust fan 455 generates airflows 1205, 1210, 1215 and 1220 which are directed into the detection chamber 905. The airflow 1225 is air pushed outside the detection level 530 through the filter 910, which purges the detection chamber 905 while expelling stuck dusts from the external surface of the filter 910. Since the exhaust fan 455 and the exhaust filter 920 are positioned above the detection chamber 905, cleaner air is pushed into the detection chamber 905.

The smoke detection sensor 410, the carbon monoxide sensor 415 and the temperature sensor 420 may be implemented using off-the-shelf components well-known in the art. The smoke detection sensor 405, the carbon monoxide sensor 415 and the temperature sensor 420 are mounted in the vicinity of the detection chamber 405 and are part of the detection level 530. The smoke detection sensor 405, the carbon monoxide sensor 415 and the temperature sensor 420 are electrically connected to the processor 405. The smoke detection sensor 405, the carbon monoxide sensor 415 and the temperature sensor 420 may receive instructions from the processor 405 to respectively detect a smoke detected measure, a carbon monoxide detected measure and a temperature detected measure. Alternatively, the smoke detection sensor 410, the carbon monoxide sensor 415 and the temperature sensor 420 may respectively measure the smoke detected measure, the carbon monoxide detected measure and the temperature detected measure either continuously, or at regular intervals so as to reduce power consumption of the detector 105.

The smoke detection sensor 410 relies on a dual-frequency band technology, described in a publication titled "Investigation of the Potential Use of Blue Light in Forward Scattering Optical Smoke Chambers to Detect all UL217 Fires in the New Standard", authored by David Richardson, Daniel O'Shea, Stephen Daniels, Michael Byrne from the Ei Electronics, of Shannon in Ireland. This article discloses improving the accuracy of smoke particles detection by using Infra-Red light and blue light. To further reduce the number and size of components in the detection level 530, the present smoke detection sensor 410 relies on a bi-color LED, to produce both the Infra-Red light and blue light.

Electronic Level 520

The electronic level 520 may be directly electrically connected with the electric connection level 510. Alternatively, the electronic level 520 may be provided with an intermediate circuit for electrically insulating the electric components of the electronic level 520, namely the processor 405, the communication module 425, the alarm module 460 and the memory 465 from the electric connection level 510.

Reference is now made concurrently to FIGS. 4 and 5. The electronic level 520 includes the processor 405, the memory 465, the communication module 425, the manual actuator 450, the exhaust fan 455 and the alarm module 460.

The processor 405 may be any type of electronic component with processing capabilities, such as for example one or several parallel general-purpose processor(s), one or several parallel microprocessor(s) or microcontroller(s), Field Programmable Gate Array(s) (FPGA), Application Specific Integrated Circuit (ASIC), etc. or a combination thereof. The processor 405 executes a computer-implemented program for controlling operations of the detector 105. The processor 405 relies on predetermined thresholds, addresses and identifiers stored in the memory 465 when executing the computer-implemented program. Although not specifically described herein, it will be apparent to those skilled in the art that the processor 405 and the memory 465 are secured to prevent physical and electronic tampering, either local or remote.

The memory 465 may be include one or several types of memory known in the electronic industry, such as for example volatile memory (Random Access Memory (RAM), etc.), and non-volatile memory (Read-Only Memory (ROM), Erasable Programmable Read-Only Memory (EPROM), Electric Erasable Programmable Read-Only Memory (EEPROM), Flash Memory, etc.) or a combination thereof. The memory 465 stores predetermined thresholds for each of the smoke detection sensor 415, carbon monoxide sensor 415 and temperature sensor 420. The memory 465 may further store a severity indicator for each predetermined threshold. The following table is an example of stored predetermined thresholds and severity indicators stored in the memory 465:

TABLE 1

| Types of threshold | Values of predetermined threshold | Severity indicator |
| --- | --- | --- |
| Smoke threshold 1 | <1% | Normal |
| Smoke threshold 2 | 1 to 7% | Abnormal |
| Smoke threshold 3 | +7 to 12.5% | High |
| Carbon monoxide threshold 1 | 0-9 PPM | Normal |
| Carbon monoxide threshold 2 | 10-24 PPM | Abnormal |
| Carbon monoxide threshold 3 | >24 PPM | High |
| Temperature threshold 1 | <40° C. | Normal |
| Temperature threshold 2 | 40-45° C. | Abnormal |
| Temperature threshold 3 | >45° C. | High |

The memory further stores the addresses and identifiers for allowing the detector 105 to communicate with the wired detectors 130a and 130b, the wireless detector 140 and the monitoring central station 160. More particularly, the memory stores the following addresses and identifiers:

TABLE 2

| Type | Description | Example |
| --- | --- | --- |
| Device ID | 8-digit number provided during production | 12345678 |
| House ID | 8-digit number shared by the other detectors 105 in the same residence. This 8-digit number is configured upon installation and corresponds to the Device ID of the first detector 105 installed in the residence. | 12345678 |
| Neighbor(s) ID(s) | 8-digit number configured upon installation. The Neighbor(s) ID(s) is automatically obtained through an advertising/response procedure described later. | 12345678 |
| Source IP Address | an IPv4 or IPv6 address obtained via a Dynamic Host Configuration Protocol procedure through Wi-Fi or a cellular network | |
| Monitoring Central Station Addresses 1 | First address to be used when communicating with the monitoring central station. Programmed before installation. The Monitoring Central Station Address 1 comprises a group of addresses, such as an IPv6 address, a cellular phone data address, and an RF proprietary address. | IPv4 or IPv6 on Transmission Control Protocol (TCP), based on standard NG9-1-1, Security Information Management Systems (SIMS) protocol or a proprietary protocol. |
| Monitoring Central Station Addresses 2 | Second address to be used when communicating with the monitoring central station. Programmed before installation. The Monitoring Central Station Address 1 comprises a group of addresses, such as an IPv6 address, a cellular phone data address, and an RF proprietary address. | IPv4 or IPv6 on Transmission Control Protocol (TCP), based on standard NG9-1-1, Security Information Management Systems (SIMS) protocol or a proprietary protocol. |
| Monitoring Central Station Addresses - Severe instances | Address to be additionally used when the severity of the alarm is high. Programmed before installation | IPv4 or IPv6 on Transmission Control Protocol (TCP), based on standard NG9-1-1, Security Information Management Systems (SIMS) protocol or a proprietary protocol. |

The communication module 425 may comprise one or several of the following modules: a 433/915 MHz wireless transceiver 430, a cellular module 435, a Wi-Fi module 440 and an RF proprietary module 445. The 433/915 MHz wireless transceiver 430, the cellular module 435, the Wi-Fi module 440 and the RF proprietary module 445 may be provided and fully configured for communication upon production of the detector 105. Alternatively, the 433/915 MHz wireless transceiver 430, the cellular module 435, the Wi-Fi module 440 and the RF proprietary module 445 may be provided upon production of the detector 105 and configured upon installation or selling of the detector 105. Additionally, the cellular module 435 may comprise an access door (not shown) for inserting a Subscriber Identity Module (SIM) card for allowing the cellular module 435 to communicate with proximate cellular antennas.

The 433/915 MHz wireless transceiver 430 is used for transceiving with proximate wireless detector(s) 140, in accordance with protocols and messages adopted by the industry. Messages exchanged on the 433/915 MHz wireless transceiver 430 are generated by the processor 405 or forwarded from the wired detectors 130a and 130b by the processor 405, and typically include the following information: the Device ID, an indication as to whether the detected measure received from the smoke detection sensor 410 is above the predetermined threshold, an indication as to whether the detected measure received from the carbon monoxide sensor 415 is above the predetermined threshold, an indication to restore the previously sent indications of detected measures received from the smoke detection sensor 410 and the carbon monoxide sensor 415, a floor in which the detected measure received is above the predetermined threshold (when available), and a room identifier in which the detected measure received above the predetermined threshold has been received (when available). To reduce consumption, the 433/915 MHz wireless transceiver 430 is powered every 5 seconds for 1 millisecond. As proximate wireless detector 140 in the vicinity typically transmits alarm messages for 11 seconds, the 433/915 MHz wireless transceiver 430 will thus have two occasions for receiving the alarm messages therefrom. In the absence of an alarm message from the proximate wireless detector 140, the 433/915 MHz wireless transceiver 430 will automatically power down after 15 seconds of silence.

The cellular module 435 communicates with the monitoring central station 160 using any known cellular standard or protocol, such as for example: GSM, UMTS, 2G, 3G, 4G, 5G, LTE or any other standard or protocol for cellular communications. To that effect, the cellular module is provided with a SIM card. The SIM card provides a unique identifier for the cellular module 435. Before delivery or upon installation of the detector 105, Monitoring Central Station Addresses 1 and Monitoring Central Station Addresses 2 are stored in the memory 465. The cellular module 435 starts communicating with the monitoring central station 160 by using the Monitoring Central Station Address 1 corresponding to the cellular module 435. When a cellular communication cannot be established using the Monitoring Central Station Address 1 corresponding to the cellular module 435, the cellular module 435 cellularly communicates with the monitoring central station 160 using the Monitoring Central Station Address 2 corresponding to the cellular module 435 stored in the memory 465. The cellular module 435 reports to the processor 405 and to the monitoring central station 160 that cellular communication using the Monitoring Central Station Address 1 corresponding to the cellular module 435 stored in the memory 465 could not be established or successfully completed. The messages generated by the processor 405 and sent by the cellular module 435 to the monitoring central station 160 may comprise: a Monitoring Central Station Address (1 or 2), a Device ID, a House ID, a battery level, a date of production of the detector, the detected measure received from the smoke detection sensor 410, the detected measure received from the carbon monoxide sensor 415, the detected temperature received from the temperature sensor 420, and any other data which may be relevant to the monitoring central station 160 for determining the best course of action. The cellular module 435 may further receive messages from the monitoring central station 160. The messages received from the monitoring central station 160 are automatically passed to the processor 405 for execution. For example, depending on the values of battery level, date of production of the detector, the detected measure received from the smoke detection sensor 410, the detected measure received from the carbon monoxide sensor 415 and the detected temperature received from the temperature sensor 420, the monitoring central station 160 may instruct the processor to actuate the exhaust fan 455 to perform one of several purging cycles before instructing the smoke detection sensor 410, the carbon monoxide sensor 415 and the temperature sensor 420 to detect new respective measures.

The Wi-Fi module 440 wirelessly communicates with the monitoring central station 160 using one of the following protocols: IPv4, IPv6, a monitoring central station specific standard protocol, an Ethernet protocol or a proprietary protocol. The Wi-Fi module 440 starts wirelessly communicating with the monitoring central station 160 by using the Monitoring Central Station Address 1 corresponding to the Wi-Fi module 440. When a wireless communication cannot be established using the Monitoring Central Station Address 1 corresponding to the Wi-Fi module 440, the Wi-Fi module 440 wirelessly communicates with the monitoring central station 160 using the Monitoring Central Station Address 2 corresponding to the Wi-Fi module 440 stored in the memory 465. The Wi-Fi module 440 reports to the processor 405 and to the monitoring central station 160 that wireless communication using the Monitoring Central Station Address 1 corresponding to the Wi-Fi module 440 stored in the memory 465 could not be established or successfully completed. The messages generated by the processor 405 and sent by the Wi-Fi module 440 to the monitoring central station 160 may comprise: a Monitoring Central Station Address (1 or 2), a Device ID, a House ID, a battery level, a date of production of the detector, the detected measure received from the smoke detection sensor 410, the detected measure received from the carbon monoxide sensor 415, the detected temperature received from the temperature sensor 420, and any other data which may be relevant to the monitoring central station 160 for determining the best course of action. The Wi-Fi module 440 may further receive messages from the monitoring central station 160. The messages received from the monitoring central station 160 are automatically passed to the processor 405 for execution. For example, depending on the values of battery level, date of production of the detector, the detected measure received from the smoke detection sensor 410, the detected measure received from the carbon monoxide sensor 415 and the detected temperature received from the temperature sensor 420, the monitoring central station 160 may instruct the processor to actuate the exhaust fan 455 to perform one of several purging cycles before instructing the smoke detection sensor 410, the carbon monoxide sensor 415 and the temperature sensor 420 to detect new respective measures.

The RF proprietary module 445 wirelessly communicates with a setup box (not shown) wired to a router, where the router communicates with the monitoring central station 160 using any type of proprietary protocol. The RF proprietary module 445 starts communicating with the monitoring central station 160 by using the Monitoring Central Station Address 1 corresponding to the RF proprietary module 445. When RF communication cannot be established using the Monitoring Central Station Address 1 corresponding to the RF proprietary module 445, the RF proprietary module 445 communicates with the monitoring central station 160 using the Monitoring Central Station Address 2 corresponding to the RF proprietary module 445 stored in the memory 465. The RF proprietary module 445 reports to the processor 405 and to the monitoring central station 160 that cellular communication using the Monitoring Central Station Address 1 corresponding to the RF proprietary module 445 stored in the memory 465 could not be established or successfully completed. The messages generated by the processor 405 and sent by the RF proprietary module 445 to the monitoring central station 160 may comprise: a Monitoring Central Station Address (1 or 2), a Device ID, a House ID, a battery level, a date of production of the detector, the detected measure received from the smoke detection sensor 410, the detected measure received from the carbon monoxide sensor 415, the detected temperature received from the temperature sensor 420, and any other data which may be relevant to the monitoring central station 160 for determining the best course of action. The RF proprietary module 445 may further receive messages from the monitoring central station 160. The messages received from the monitoring central station 160 are automatically passed to the processor 405 for execution. For example, depending on the values of battery level, date of production of the detector, the detected measure received from the smoke detection sensor 410, the detected measure received from the carbon monoxide sensor 415 and the detected temperature received from the temperature sensor 420, the monitoring central station 160 may instruct the processor to actuate the exhaust fan 455 to perform one of several purging cycles before instructing the smoke detection sensor 410, the carbon monoxide sensor 415 and the temperature sensor 420 to detect new respective measures.

Although described as functioning independently in the previous paragraphs, the cellular module 435, the Wi-Fi module 440 and the RF proprietary module 445 could in fact be used concurrently to establish a communication with the monitoring central station 160 in the most efficient manner. Upon successful establishment of the communication by one of the cellular module 435, the Wi-Fi module 440 and the RF proprietary module 445, the processor 405 may instruct the other modules to abort their effort of establishing a communication with the monitoring central station 160.

Alternatively, the cellular module 435, the Wi-Fi module 440 and the RF proprietary module 445 could be configured to communicate with different instances of monitoring central stations 160, depending on the severity of alarm, the severity of the situation etc. For doing so, the processor 405 may first instruct the Wi-Fi module 440 to establish a communication with a first instance of monitoring central station 160, such as for example a security agency or a proprietary web service for low and medium severity alarms or low and medium severe situations. Should the situation escalate, or the alarm becomes high severity, the processor 405 may then additionally instruct the cellular module 435 to communicate with a second instance of monitoring central station 160, such as for example an emergency dispatch office or a public-safety answering point. In the event that the processor 405 determines that the detected measures warrant contacting directly a most proximate fire station, the processor 405 then instructs the RF proprietary module 445 to immediately communicate with the most proximate fire station, which coordinates may be stored in the memory 465 of the detector 105 for example upon installation, or remotely stored in the memory 465 of the detector 105 by the proprietary web service or security agency upon subscription to the service, or using an application installed on a mobile device (not shown) which communicates the processor 405 using an appropriate protocol and security level.

The processor 405 is also electrically connected to the data link 125 and receives the alarms from the wired detectors 130a and 130b electrically interconnected therewith. The processor 405 may also forward an alarm locally generated by the processor 405 or received through the 433/915 MHz wireless transceiver 430 to the wired detectors 130a and 130b on the data link 125. Messages exchanged through the data link 125 typically include: an indication that the detected measure received from the smoke detection sensor 410 is above a predetermined threshold, an indication that the detected measure received from the carbon monoxide sensor 415 is above a predetermined threshold, and an indicator that the detected measure received from the smoke detection sensor 410 and the carbon monoxide sensor 415 are below the predetermined threshold.

The manual actuator 450 is mechanically connected directly or indirectly with the processor 405. The manual actuator 450 may consist for example of a button or a switch, provided on an exterior surface of the detector 105, to request the processor to temporarily deactivate the alarm module 460, and to postpone initiating communication with the monitoring central station 160. In the event that the communication with the monitoring central station 160 has already been established by the communication module 425, the processor 405 generates a message indicative of the reset for temporarily deactivating the alarm and request the module 435, 440 or 445 currently in communication with the detector 105 to transmit the message indicative of the reset. Alternatively, or concurrently, the processor 405 could send the message indicative of the reset through the data link 125 to the wired detectors 130a and 130b, and through the 433/915 MHz wireless transceiver 430 to the wireless detector 140.

Figure 13:
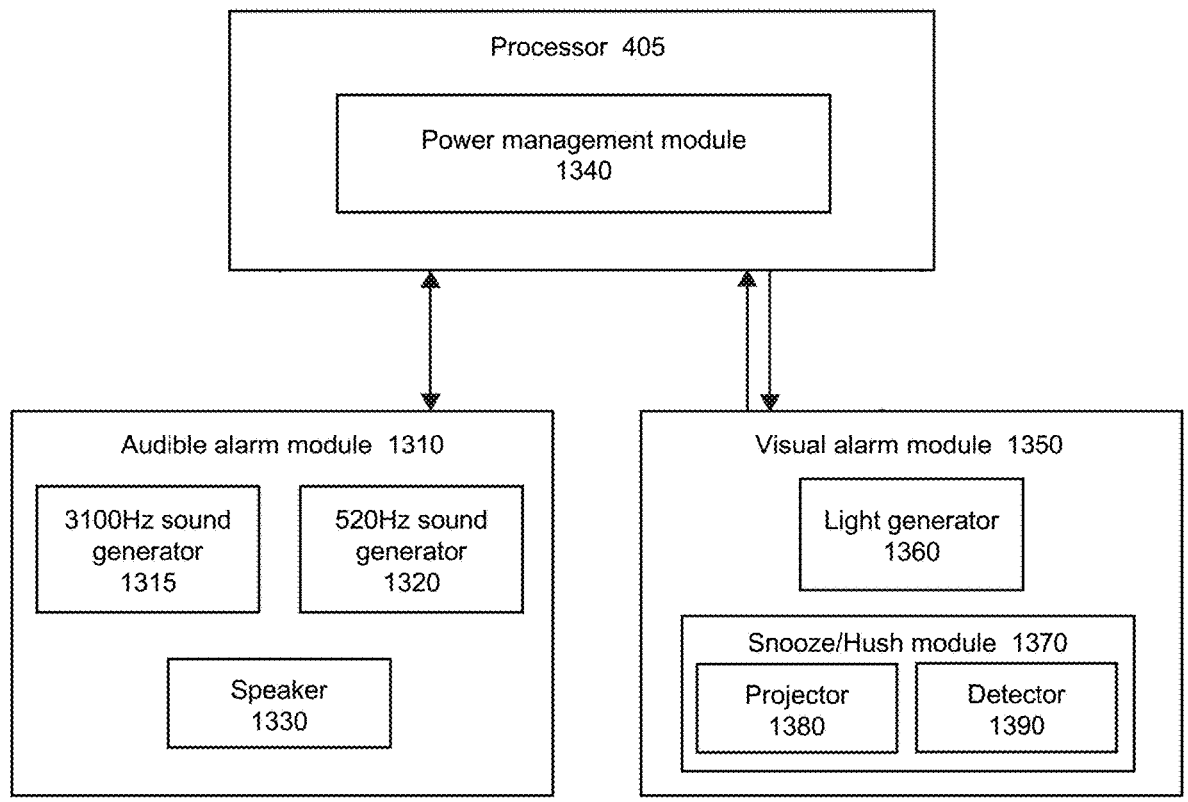
FIG. 13 is block diagram of components of the alarm module 460.

Reference is now concurrently made to FIGS. 4 and 13, where FIG. 13 is a block diagram of components of the alarm module 460. The alarm module 460 is controlled by the processor 405 and is adapted for generating an audible alarm signal and a visual alarm signal, either independently or concurrently. The alarm module 460 comprises an audible alarm module 1310 and a visual alarm module 1350. The audible alarm module 1310 comprises a 3100 Hz sound generator 1315 for generating a 3100 Hz alarm signal, a 520 Hz sound generator 1320 for generating a 520 Hz alarm signal and a speaker 1325 for converting the 3100 Hz alarm signal and the 520 Hz alarm signal into audible alarm signals. The 3100 Hz sound generator 1315, the 520 Hz sound generator 1320 and the speaker 1330 are incorporated inside the detector 105. The speaker 1330 is a built-in speaker, including a resonance chamber and an audio amplifier. The audible alarm module 1310 is implemented so as generate an audible audio signal of more than 85 dBA for the 520 Hz alarm signal. The 520 Hz alarm signal is a square wave signal which is recognized as the most effective frequency/pattern for asleep and hearing-impaired occupants.

Due to its high-power consumption, the 520 Hz sound generator 1320 further relies on a power management module 1340 executed by the processor 405, to control power consumption from the AC power and batteries of the detector 105 when the 520 Hz sound generator 1320 is actuated. The power management module 1340 controls the power consumed by the detector 105, but more precisely the power consumed by the detector 105 when the 520 Hz sound generator 1320 is actuated, so as to ensure that the 520 Hz sound generator 1320 is actuated so as to efficiently use the power available to the detector 105, provided by the AC power and/or the batteries in the detector 105.

The processor 405 controls the actuation of the audible alarm module 1310, and more precisely the actuation of the 3100 Hz sound generator 1315 and the 520 Hz sound generator 1320. The processor 405 may actuate the 3100 Hz sound generator 1315 and the 520 Hz sound generator 1320 separately or alternately.

The processor 405 further receives through the communication module 425 audible alarm instructions from the monitoring central station 160. For example, the monitoring central station 160 may instruct the processor 405 to actuate the audible alarm module 1310 and instructs the processor 405 the audible alarm signal to be used. The monitoring central station 160 may also instruct the processor 405 to use an audible alarm signal provided by the monitoring central station 160 through the communication module 425.

The visual alarm module 1350 generates when actuated by the processor 405 the visual alarm signal. The visual alarm module 1350 comprises a light generator 1360 and a snooze/hush module 1370. The light generator 1360 may comprise one or several lights, such as for example Light Emitting Diode(s). The light generator 1360 generates the visual alarm signal as instructed by the processor 405. For example, the processor 405 may instruct the light generator 1360 to actuate one or several lights separately, concurrently or alternately.

For example, the visual alarm module 1350 could include a first light source for generating a pulsed visual alarm signal when less severe instance of alarm is detected, a second light source for generating a continuous alarm signal when a more important instance of alarm is detected, and a third light source for generating a strong stroboscopic visual alarm when a severe instance of alarm is detected. Providing multiple visual alarm signals allows the occupants in a room where the visual alarm signal is generated to evaluate the severity of the detected alarm and act accordingly. For example, burned toasts could warrant a visual alarm signal corresponding to the less severe instance, while a fire causing heavy smoke would warrant a severe alarm and thus a stroboscopic visual alarm signal.

The light generated by the visual alarm module 1350 could further encourage and facilitate evacuation by generating light at a lower but constant intensity. Intensity and color of the light generated by the light generator 1360 could further be adapted by the processor 405 to adapt to the conditions detected by the smoke detection sensor 410, the carbon monoxide sensor 415 and the temperature sensor 420. Adapting the visual alarm generated by the visual alarm module 1350 increases the security provided by the detector 105 while improving the environmental conditions for facilitating evacuation.

Figure 14:
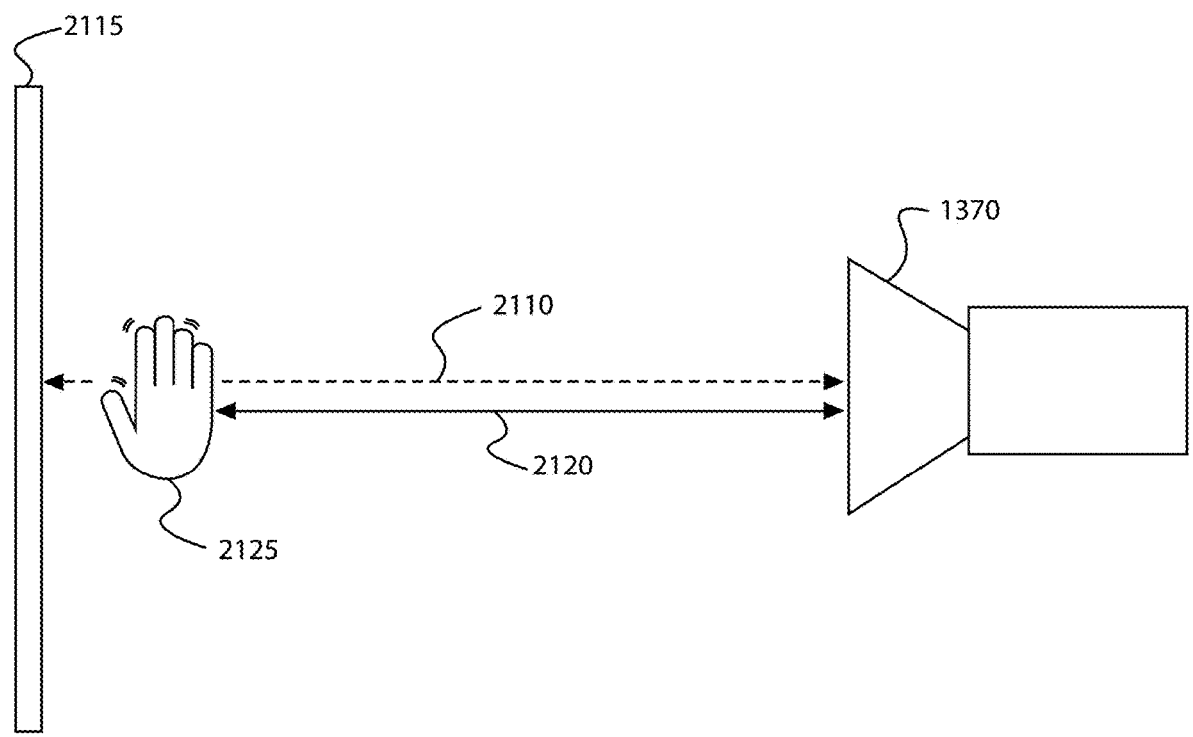
FIG. 14 shows an example operation of a snooze/hush module.

Reference is now further concurrently made to FIG. 14, where FIG. 14 depicts exemplary operation of the snooze/hush module 1365. The snooze/hush module 1365 provides a mechanism for hushing or snoozing the audible alarm module 1310. The snooze/hush module 1365 projects a light signal 1410 on a wall adjacent to the detector 105 and detects 1420 presence or movement in a line of projection of the light signal projected. The light signal projected 1410 may be any type of light signal that could be projected on a wall, such as for example: a projected image, a projected image of a word, a projected message, etc. The light signal may be projected by an LED, a laser or a tiny bulb, with or without the use of lenses, masks and/or gratings. The light signal may be constant or pulsed, of one color or varying color. The processor 105 instructs the generation of the light signal by the snooze/hush module 1365. The processor 105 can adapt the light signal generated by the snooze/hush module 1365 as a function of the conditions detected by the smoke detection sensor 410, the carbon monoxide sensor 415 and the temperature sensor 420. For example, the processor 105 instructs the snooze/hush module 1365 to project different words depending on the conditions detected: "smoke" when the detected measure received from the smoke detection sensor 410 is above the predetermined threshold, "carbon monoxide" when the predetermined measure received from the carbon monoxide sensor 415 is above the predetermined threshold, and "heat" when the detected measure received from the temperature sensor 420 is above the predetermined threshold. Furthermore, when the detected measure received by any of the smoke detection sensor 410, the carbon monoxide sensor 415 and the temperature sensor 420 is over a predetermined threshold that is considered concerning, the processor 105 instructs the snooze/hush module 1365 to project "evacuate immediately". The light signal projected 1410 may rely on any technology known for projecting images and words on a proximate surface, such as for example prisms, filters and/or masks.

The snooze/hush module 1365 further detects 1420 presence or movement in a line of projection of the light signal projected 1410. For doing so, the snooze/hush module 1365 may rely on a depth sensor for detecting a change in distance between the depth sensor and the light signal projected 1410, a heat sensor capable of detecting presence of body heat within the line of projection of the light signal projected 1410, or a camera pointing at the light signal projected 1410 and capable of detecting loss (or partial loss) of the light signal projected 1410. When presence of movement is detected 1420 in the line of projection of the light signal projected 1410, the snooze/hush module 1365 reports the detected presence or movement to the processor 105. Upon receipt of the detected 1420 presence or movement in the line of projection of the light signal projected 1410 by the snooze/hush module 1365, the processor temporarily deactivates the audible alarm module 1310. The processor 105 also starts a predetermined timer, to restart the audible alarm module 1310 if the detected measures received from the smoke detection sensor 410, the carbon monoxide sensor 415 and the temperature sensor 420 are not below the predetermined threshold at the expiration of the predetermined time. Upon detection 1420 of the presence or movement in the line of projection of the light signal projected 1410, the processor 105 may further actuation of the exhaust fan 455 for a predetermined interval which is less than the predetermined timer.

Although not specifically mentioned, implementation of the present detector 105, sequence and timing of tasks performed by the processor 105 are performed in conformity with applicable UL/Underwriters Laboratories of Canada (ULC) standards.

Detector Actuation

Upon powering up, the processor 405 starts executing the computer-implemented program stored in the memory 465. The processor 405 further extracts the identifiers and addresses of Table 2. The processor 405 then proceeds with performing a verification of proper operation of the detection level 530, and more precisely, requesting the smoke detection sensor 410, the carbon monoxide sensor 415 and the temperature sensor 420 to take respective measurements. The smoke detection sensor 410 proceeds with taking a detected measure of the quantity of smoke particles present in the detection chamber 905, and returns the detected smoke measure to the processor 405. The carbon monoxide detector 415 proceeds with measuring the quantity of carbon monoxide in the detection chamber 905 and returns the detected carbon monoxide measure to the processor 405. The temperature sensor 420 proceeds with measuring the temperature in the detection chamber 905 and returns the detected temperature to the processor 405.

The processor 405 compares the detected measure received from the smoke detection sensor 410 and the predetermined value for smoke threshold (see table 1), compares the detected measure received from the carbon monoxide sensor 415 with the predetermined value for carbon monoxide threshold (see table 1), compares the detected measure received from the temperature sensor 420 and the predetermined value for the temperature threshold (see table 1), and determines whether the detected measure received from the smoke detection sensor 410, the carbon monoxide sensor 415 and the temperature sensor 420 are below their predetermined thresholds. If one of the detected measures from the smoke detection sensor 410, the carbon monoxide sensor 415 and the temperature sensor 420 are not below the predetermined values, the processor 405 instructs the exhaust fan 455 to perform a purge of the content of the detection chamber 905 by actuating the exhaust fan 455 to operate for a certain period of time at a certain speed. After the purge of the content of the detection chamber 905 has been completed, the processor 405 instructs the smoke detection sensor 410, the carbon monoxide sensor 415 and the temperature sensor to take respective second measurements and report the respective measurements. If the respective second measurements of the smoke detection sensor 410, the carbon monoxide sensor 415 and the temperature sensor 420 are not below their predetermined respective thresholds, the processor 405 instructs the visual alarm module 1350 to generate a visual alarm signal indicating that the detector 105 is malfunctioning and needs to be replaced.

Detector Operation

In operation, the processor 405 instructs the smoke detection sensor 410, the carbon monoxide sensor 415 and the temperature sensor 420 to take measurements of the amount of smoke particles, the amount of carbon monoxide and the temperature in the detection chamber 905 respectively. The instruction to take measurements is generated and sent periodically by the processor 405 at a predetermined interval. However, when the processor 405 determines that one of the detected measures received from the smoke detection sensor 410, the carbon monoxide sensor 415 and/or the temperature sensor 420 is above one of the predetermined thresholds, such as for example the predetermined thresholds identified in Table 1 above, the processor 405 enters into a level 1 alarm mode. In level 1 alarm mode, the processor 405 reduces the predetermined interval for taking measurements by the smoke detection sensor 410, the carbon monoxide sensor 415 and the temperature sensor 420.

The processor 405 further instructs the exhaust fan 455 to purge the content of the detection chamber 905 by actuating the exhaust fan 455 at a certain speed for a period of time. After the exhaust fan 455 has completed the purge of the detection chamber 905, the processor 405 instructs the smoke detection sensor 410, the carbon monoxide sensor 415 and the temperature sensor 420 to take measurements. If all the detected measures received from the smoke detection sensor 410, the carbon monoxide sensor 415 and the temperature sensor 420 are below their respective threshold 1 levels (for example refer to Table 1), the processor 405 returns to a level 0 alarm mode. Table 3 below provides examples of the various levels of alarms, and the corresponding operations undertaken by the processor 405.

TABLE 3

| Alarm level (severity) | Condition(s) | Processor Operations |
| --- | --- | --- |
| 0 - normal mode | Detected measures received from the smoke detection sensor 410, the carbon monoxide sensor 415 and the temperature sensor 420 are below their respective thresholds 1 level. | Processor 405 continues generating and sending of instruction message to take measurements at predetermined interval. |
| 1 - unconfirmed alarm detected | At least one of the detected measures received from the smoke detection sensor 410, the carbon monoxide sensor 415 and the temperature sensor 420 is/are above their respective thresholds level 1. | Processor 405 instructs the exhaust fan 455 to purge the detection chamber 905, and after purge is completed sends instruction message to take second measurements. If at least one of the second measurements is above the respective threshold level 1, the level of alarm is raised to 2. If none of the second measurements are above the respective threshold level 1, the level of alarm is returned to 0. |
| 2 - confirmed alarm detected | Confirmed detected measure received from one of the smoke detection sensor 410, the carbon monoxide sensor 415 and the temperature sensor 420 above one of the predetermined respective thresholds. | Processor 405 continues generating and sending of instruction message to take measurements at a fraction of the predetermined interval. Processor 405 generates message to be communicated to the monitoring central station 160, and forwards the alarm information to the wireless detector 140 and the wired detectors 130a and 130b. Processor 405 actuates the alarm module 460 to generate the audible alarm signal and the visual alarm signal. |
| 3 - confirmed important alarm detected | Confirmed detected measure received from one of the smoke detection sensor 410, the carbon monoxide sensor 415 and the temperature sensor 420 above one of the predetermined respective level 2 thresholds. | Processor 405 continues generating and sending of instruction message to take measurements at a fraction of the predetermined interval. Processor 405 generates an alarm message to be communicated to the monitoring central station 160, and forwards the alarm information to the wireless detector 140 and the wired detectors 130a and 130b. Processor 405 actuates the alarm module 460 to generate the audible alarm signal and the visual alarm signal. The processor 405 instructs the visual alarm module 1350 to generate a visual alarm indicative of an order or evacuation. |

TABLE 3-continued

| Alarm level (severity) | Condition(s) | Processor Operations |
|---|---|---|
| 4 - confirmed severe alarm detected | Confirmed detected measure received from one of the smoke detection sensor 410, the carbon monoxide sensor 415 and the temperature sensor 420 above one of the predetermined respective level 3 thresholds. | Processor 405 continues generating and sending of instruction message to take measurements at a fraction of the predetermined interval. Processor 405 generates an alarm message to be communicated to the monitoring central station 160, and forwards the alarm information to the wireless detector 140 and the wired detectors 130a and 130b. Processor 405 actuates the alarm module 460 to generate the audible alarm signal and the visual alarm signal. The processor 405 instructs the visual alarm module 1350 to generate a visual alarm indicative of an order or evacuation. The processor 405 further generates and sends an alarm message to be communicated directly to the nearest fire department through the communication module 425. |

The present detector 105 thus provides an efficient solution to current fire detectors, while increasing the flexibility and safety options of currently available detectors. The present detector 105 easily wirelessly connects with the monitoring central station 160, by supporting multiple communication technologies. The present detector 105 also significantly reduces false alarms by relying one or several of the following improvements: incorporation of the exhaust fan 455, adding of the Dutch weave wire cloth 910, and purging of the detection chamber 905 upon first detection of a measure received from one of the smoke detection sensor 410, the carbon monoxide sensor 415 and the temperature sensor 420. The addition of the multiple mating connectors and protection mechanism further adds to the flexibility of the present detector 105, without negatively impacting its safety.

Figure 15:
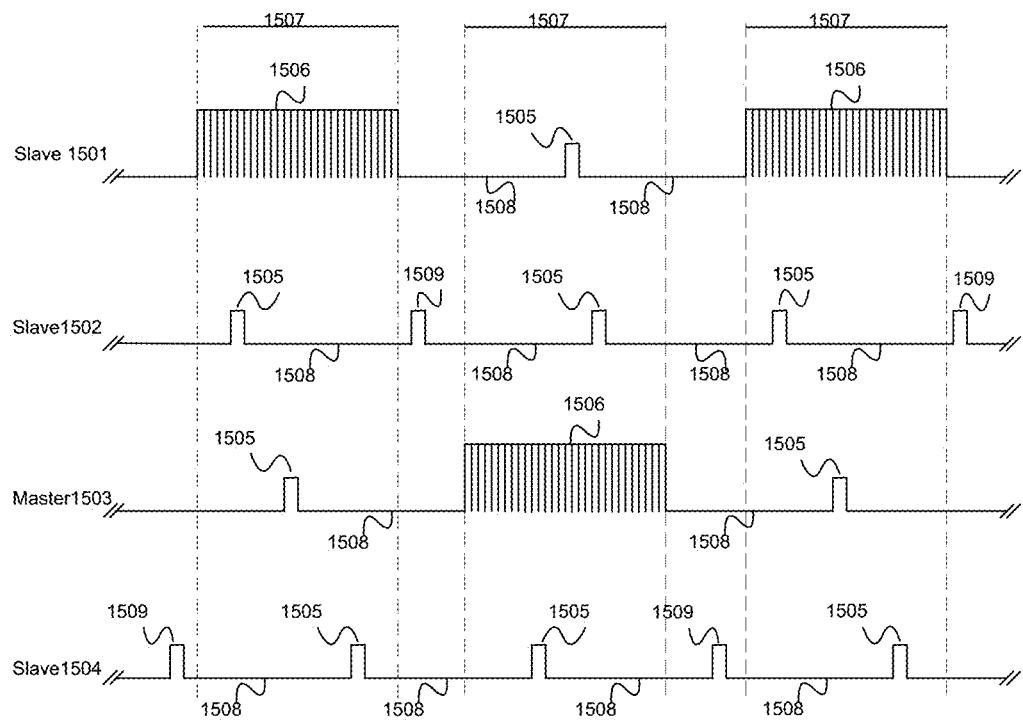
FIG. 15 is a timeflow of a low energy 433/915 MHz RF communications of a general alarm initiated by a sloave unit and rebroadcasted by the master unit.

Reference is now made to FIG. 15, which is a timeflow of a low energy 433/915 MHz RF communications of a general alarm initiated by a sloave unit and rebroadcasted by the master unit. Slave unit 1501 transmits a set of repeated alarms 1506 for the duration 1507. Slaves 1502 and 1504 as well as master 1503 initiate a listen event 1505 and 1509 at regular interval 1508. Master 1503 retransmits 1506 for the duration 1507. Salve 1501 retransmits its alarm 1506 after two snoozing periods 1508 and one listen event 1505. Snoozing periods 1508 are meant to be, but not limited to, 5 seconds. Alarm duration 1507 are meant to be, but not limited to, 6 seconds. Alarm duration 1507 must be higher than snoozing period 1508. Listen events 1509 are those outside the alarm periods whereas listen events 1505 are those within alarm periods.

Figure 16:
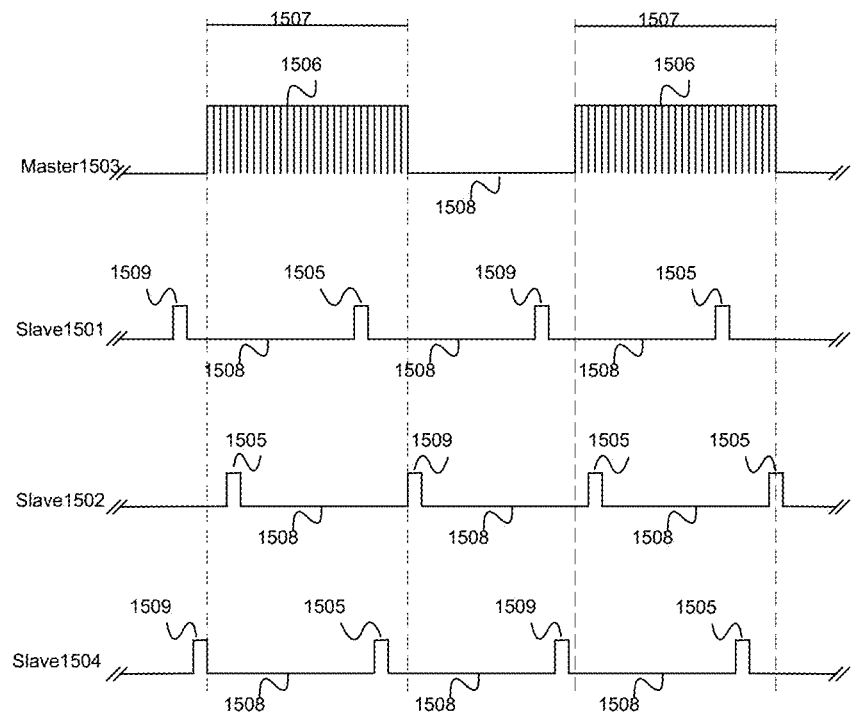
FIG. 16 is a timeflow diagram of a low energy 433/915 MHz RF communications of a general alarm initiated by the master unit.

Reference is now made to FIG. 16, which is a timeflow of a low energy 433/915 MHz RF communications of a general alarm initiated by the master unit. In this timeflow, master unit 1503 transmits a set of repeated alarms 1506 for a duration 1507. The master unit 1503 retransmits 1506 for the duration 1507 after snoozing period 1508. Snoozing periods 1508 are meant to be, but not limited to, 5 seconds. Alarm duration 1507 are meant to be, but not limited to, 6 seconds. Alarm duration 1507 must be higher than snoozing period 1508. Listen events 1509 are those outside the alarm periods whereas listen events 1505 are those within alarm periods.

Although the present disclosure has been described hereinabove by way of non-restrictive, illustrative embodiments thereof, these embodiments may be modified at will within the scope of the appended claims without departing from the spirit and nature of the present disclosure.

What is claimed is:
1. A detector comprising:
a detection level, the detection level comprising a detection chamber and at least one of a smoke detection sensor, a carbon monoxide sensor and a temperature sensor, the at least one smoke detection sensor, carbon monoxide sensor and temperature sensor generating a detected measure;
a fan for forcing air in the detection chamber; and
an electronic level, the electronic level including:
a communication module to wirelessly communicate with a monitoring central station; and
a processor for:
receiving the detected measure;
comparing the detected measure with a predetermined threshold;
upon determination that the detected measure is above the predetermined threshold, actuating the fan for a predetermined period of time and requesting the at least one smoke detection sensor, carbon monoxide sensor and temperature sensor to generate a second detected measure;
receiving the second detected measure;
comparing the second detected measure with the predetermined threshold; and
upon determination that the second detected measure is above the predetermined threshold, and generating a message to be wirelessly communicated to the monitoring central station by the communication module, the message including the second detected measure and a unique identifier of the detector.

2. The detector of claim 1, wherein:
the communication module comprises a cellular module;
the unique identifier of the detector is one of: an 8-digit Device ID, an IPv6 address, and a Subscriber Identity Module (SIM); and
the communication module wirelessly communicates with the monitoring central station using one of the following: GSM, 2G, 3G, 4G, 5G, or LTE.

3. The detector of claim 2, further comprising:
a memory for storing a first phone number for the monitoring central station; and wherein:
the cellular module communicates with the monitoring central station using the first phone number.

4. The detector of claim 3, wherein:
the memory further stores a second phone number for the monitoring central station;
the cellular module communicates with the monitoring central station using the second phone number when a communication with the monitoring central station using the first phone number is not established; and
the cellular module reports to the processor that the communication using the first phone number for the monitoring central station is not established.

5. The detector of claim 1, wherein:
the communication module comprises a Wi-Fi module;
the unique identifier of the detector is at least one of: an 8-digit Device ID and an IPv6 address;
the detector further comprises a memory for storing an IP address for the monitoring central station; and
the communication module wirelessly communicates with the monitoring central station using one of the following protocols: IPv4, IPv6, a monitoring central station standard protocol, an Ethernet protocol or a proprietary protocol.

6. The detector of claim 1, further comprising:
a 433/915 MHz wireless transceiver for wireless communicating with at least one wireless detector in a vicinity of the detector, the 433/915 MHz transceiver receives from the at least one wireless detector a wireless alarm message; and
wherein the processor receives the wireless alarm message, and upon receipt of the wireless alarm message actuates the alarm module and generates a message to be wirelessly communicated to the monitoring central station by the communication module, the message including the wireless alarm message and the unique identifier of the detector.

7. The detector of claim 1, further comprising a connection level, the connection level comprising:
a connector plane for connecting the detector to an electrical power source and to a data link, the connector plane providing a plurality of protruding electric conducive sets of pins;
a connector plate defining a plurality of connector receptacles, each connector receptacle having a set of apertures for receiving therethrough respective electric conducive sets of pins of the connector plane and electrically connecting therein corresponding mating connectors; and
a mechanical protection mechanism for allowing access to only one mating connector.

8. The detector of claim 7, wherein the mating connectors of the connector plate comprise at least two of the following: a mating connector for a legacy Kidde™ pigtail, a mating connector for a 2014 or more recent Kidde™ pigtail, a mating connector for a Firex™ pigtail, a mating connector for a BRK™ pigtail, a mating connector for a First Alert™ pigtail, a mating connector for a Dicon™ pigtail and a mating connector for an American Sensor™ pigtail.

9. The detector of claim 7, wherein:
at least one wired detector is electrically connected to the detector through the mating connector;
the processor receives a wired alarm message from the wired detector through the mating connector, and upon receipt of the wired alarm message actuates the alarm module and generates a message to be wirelessly communicated to the monitoring central station by the communication module, the message including the wired alarm message and the unique identifier of the detector.

10. The detector of claim 1, wherein:
the detection chamber is surrounded by a Dutch weave wire cloth.

11. The detector of claim 1, further comprising an alarm module to generate at least one of an audible alarm signal or a visual alarm signal; wherein upon determination that the second detected measure is above the predetermined threshold, the processor actuates the alarm module.

12. The detector of claim 1, wherein:
the detection level comprises the smoke detection sensor, the carbon monoxide sensor and the temperature sensor, the smoke detection sensor generating a smoke detected measure, the carbon monoxide sensor generating a carbon monoxide detected measure and the temperature sensor generating a temperature detected measure; and
the processor receives the smoke detected measure, the carbon monoxide detected measure and the temperature detected measured; the processor compares the smoke detected measure with a predetermined smoke threshold, compares the carbon monoxide detected measure with a predetermined carbon monoxide threshold, compares the temperature detected measure with a predetermined temperature threshold; the processor actuates the fan for a predetermined period of time and requests the smoke detection sensor, the carbon monoxide sensor and the temperature sensor to respectively generate a second smoke detected measure, a second carbon monoxide detected measure and a second temperature detected measure when: the smoke detected measure is above the smoke threshold, or the carbon monoxide detected measure is above the carbon monoxide threshold or the temperature detected measure is above the predetermined temperature threshold: the processor receives the second smoke detected measure, the second carbon monoxide detected measure and the second temperature detected measure; the processor compares the second smoke detected measure with the predetermined smoke threshold, compares the second carbon monoxide detected measure with the predetermined carbon monoxide threshold, compares the second temperature detected measure with the predetermined temperature threshold; the processor actuates the alarm module and generates the message to be wirelessly communicated to the monitoring central station by the communication module when: the second smoke detected measure is above the smoke threshold, or the second carbon monoxide detected measure is above the carbon monoxide threshold or the second temperature detected measure is above the predetermined temperature threshold; the message including the second smoke detected measure, the second carbon monoxide detected measure, the second temperature detected measure and the unique identifier of the detector.

13. The detector of claim 1, wherein:

the communication module further receives instructions from the monitoring central station and forwards the instructions to the processor;

the processor processes the instructions received from the monitoring central station and generates a reporting message; and the communication module communicates the reporting message to the monitoring central station.

14. The detector of claim 1, wherein the detector communicates with both a local monitoring central station and a remote monitoring central station.

15. The detector of claim 1, wherein the audible alarm signal is a 520 Hz fire alarm sound and the visual alarm signal is a light pattern.

16. The detector of claim 1, wherein the smoke detection sensor is adapted for generating a detected measure of a quantity of smoke particles present in the detection chamber.

17. The detector of claim 1, wherein the carbon monoxide sensor is adapted for generating a detected measure of a quantity of carbon present in the detection chamber.

18. The detector of claim 1, wherein the temperature sensor is adapted for generating a detected measure of a temperature in the detection chamber.

19. The detector of claim 1, further comprising:

a 433/915 MHz wireless transceiver for wireless communicating with at least one wireless detector in a vicinity of the detector; and wherein the 433/915 MHz wireless transceiver transmits the message to the at least one wireless detector.

20. The detector of claim 7, wherein:

at least one wired detector is electrically connected to the detector through the mating connector and the processor transmits the message to the at least one wired detector through the mating connector.

* * * * *